US006274560B1

(12) United States Patent
Khosla et al.

(10) Patent No.: US 6,274,560 B1
(45) Date of Patent: Aug. 14, 2001

(54) CELL-FREE SYNTHESIS OF POLYKETIDES

(75) Inventors: Chaitan Khosla, Stanford, CA (US); Rembert Pieper, Washington, DC (US); Guanglin Luo, Madison, CT (US); David E. Cane, Providence, RI (US); Camilla Kao, Palo Alto, CA (US)

(73) Assignees: Brown University Research Foundation, Providence, RI (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/374,711

(22) Filed: Aug. 13, 1999

Related U.S. Application Data

(62) Division of application No. 08/675,817, filed on Jul. 5, 1996, now Pat. No. 6,080,555.
(60) Provisional application No. 60/003,338, filed on Jul. 6, 1995.

(51) Int. Cl.$^7$ ..................................................... C12N 15/76
(52) U.S. Cl. ........................ 514/29; 435/471; 435/252.3; 435/252.35; 435/320.1
(58) Field of Search ................................ 435/41, 7.1, 64, 435/471, 252.3, 252.35, 320.1; 514/29

(56) References Cited

U.S. PATENT DOCUMENTS

| | | |
|---|---|---|
| 5,475,099 | 12/1995 | Knauf et al. . |
| 5,824,513 | 10/1998 | Katz et al. ............................. 435/76 |
| 5,842,513 | 10/1998 | Katz . |
| 6,004,787 | 12/1999 | Katz et al. ........................... 435/183 |
| 6,060,234 | 5/2000 | Katz et al. ............................... 435/4 |
| 6,063,561 | 5/2000 | Katz et al. ............................... 435/4 |
| 6,080,555 | 6/2000 | Khosla et al. ......................... 435/41 |

FOREIGN PATENT DOCUMENTS

| | | |
|---|---|---|
| WO 93/13663 | 7/1993 | (WO) . |
| WO 97/02358 | 1/1997 | (WO) . |
| WO 97/13845 | 4/1997 | (WO) . |
| WO 98/01546 | 1/1998 | (WO) . |
| WO 98/01571 | 1/1998 | (WO) . |

OTHER PUBLICATIONS

Bedford et al., "A Functional Chimeric Modular Polyketide Synthase Generated via Domain Replacement," Chemistry & Biology (1996) 3(10):827–831.
Cane et al., "Macrolide Biosynthesis. 7. Incorporation of Polyketide Chain Elongation Intermediates into Methymycin," J Am Chem Soc (1993) 115:522–526.
Cortes et al., "Repositioning of a Domain in a Modular Polyketide Synthase to Promote Specific Chain Cleavage," Science (1995) 268:1487–1489.
Daum et al., "Mutational Biosynthesis of New Antibiotics," Ann Rev Microbiol (1979) 33:241–265.

Donadio et al., "Biosynthesis of the Erythromycin Macrolactone and a Rational Approach for Producing Hybrid Macrolides," Gene (1992) 115:97–103.
Donadio et al., "An Erythromycin Analog Produced by Reprogramming of Polyketide Synthesis," Proc Natl Acad Sci USA (1993) 90:7119–7123.
Dutton et al., "Avermectin Biosynthesis. Intact Incorporation of a Diketide Chain–Assembly Intermediate into the Polyketide Macrocycle Ring," Tetrahedron Letters (1994) 35(2):327–330.
Dutton et al., "Novel Avermectins Produced by Mutational Biosynthesis," J Antibiot (1991) 44(3):357–365.
Gokhale et al., "Functional Orientation of the Acyltransferase Domain in a Module of the Erythromycin Polyketide Synthase," Biochemistry (1998) 37:2524–2528.
Kao et al., "Gain of Function Mutagenesis of the Erythromycin Polyketide Synthase. 2. Engineered Biosynthesis of an Eight–Membered Ring Tetraketide Lactone," J Am Chem Soc (1997) 119(46):11339–11340.
Kao et al., "Manipulation of Macrolide Ring Size by Directed Mutagenesis of a Modular Polyketide Synthase," J Am Chem Soc (1995) 117(35):9105–9106.
Kao et al., "Evidence for Two Catalytically Independent Clusters of Action Sites in a Functional Modular Polyketide Synthase," Biochemistry (1996) 35(38):12363–12368.
Kao et al., "Engineered Biosynthesis of Structurally Diverse Tetraketides by a Trimodular Polyketide Synthase," J Am Chem Soc (1996) 118(38):9184–9185.
Kramer et al., "Rational Design and Engineered Biosynthesis of a Novel 18–Carbon Aromatic Polyketide," J Am Chem Soc (1997) 119(4):635–639.
Kuhstoss et al., "Production of a Novel Polyketide Through the Construction of a Hybrid Polyketide Synthase," Gene (1996) 183:231–236.
McDaniel et al., "Gain–of–Function Mutagenesis of a Modular Polyketide Synthase," J Am Chem Soc (1997) 119(18):4309–4310.
Oliynyk et al., "A Hybrid Modular Polyketide Synthase Obtained by Domain Swapping," Chem Biol (1996) 3(10):833–839.
Pereda et al., "The Loading Domain of the Erythromycin Polyketide Synthase is not Essential for Erythromycin Biosynthesis in *Saccharopolyspora erythraea*," Microbiology (1998) 144:543–553.
Pieper et al., "Remarkably Broad Substrate Specificity of a Modular Polyketide Synthase in a Cell–Free System," J Am Chem Soc (1995) 117(45):11373–11374.

(List continued on next page.)

*Primary Examiner*—Laurie Scheiner
(74) *Attorney, Agent, or Firm*—Morrison & Foerster LLP

(57) ABSTRACT

Cell-free systems which effect the production of polyketides employing modular polyketide synthases are described. Libraries of new and/or known polyketides may also be produced in cell-free systems employing aromatic PKS, modular PKS or both.

13 Claims, 6 Drawing Sheets

OTHER PUBLICATIONS

Pieper et al., "Cell–Free Synthesis of Polyketides by Recombinant Erythromycin Polyketide Synthesis," Nature (1995) 378:263–266.

Pieper et al., "Purification and Characterization of Bimodular and Trimodular Derivatives of the Erythromycin Polyketide Synthase," Biochemistry (1997) 36(7):1846–1851.

Pieper et al., "Erythromycin Biosynthesis: Kinetic Studies on a Fully Active Modular Polyketide Synthase Using Natural and Unnatural Substrates," Biochemistry (1996) 35:2054–2060.

Wiesmann et al., "Polyketide Synthesis In Vitro on a Modular Polyketide Synthase," Chem Biol (1995) 2(9):583–589.

Aparicio et al., J. of Biol. Chem. (1994), 269(11):8524–8528.

Bartel et al., J. Bacteriol (1990), 172(9):4816–4826.

Beck et al., Eur. J. Biochem. (1990), 192:487–498.

Bevitt et al., Eur. J. Biochem. (1992), 204:39–49.

Bibb et al., EMBO J. (1989), 8(9):2727–2736.

Caballero et al., Mol. Gen. Genet. (1991), 230:401–412.

Caffrey et al., Eur. J. Biochem.(1991), 195:823–830.

Caffrey et al., FEBS Lett. (1992), 304:225–228.

Corcoran et al., 5th International Congress of Chemotherapy, Vienna, Abstracts of Communications (1967) pp:35–40.

Corcoran, ed. in *Antibiotics vol. IV Biosynthesis*, Springer–Verlag, NY, pp. 145–50 (1982).

Cortes et al., Nature (1990), 348:176–178.

Davis et al., Abst. of the Genetics of Industrial Microorganisms Mtg. (1994), P288:192.

Dimroth et al., Eur. J. Biochem. (1970), 13:98–110.

Donadio, S., et al., Science (1991), 252:675–679.

Donadio et al., Gene (1992), 111:51–60.

Fernandez–Moreno et al., Cell (1991), 66:769–780.

Fernandez–Moreno et al., J. Biol. Chem. (1992), 267:19278–19290.

Hallam et al., Gene (1988), 74:305–320.

Hopwood et al., Nature (1985), 314(6012):642–644.

Hopwood et al., (1992) Secondary Metabolites: Their Function and Evolution, Wiley Chichester (Ciba Foundation Symposium 171), pp:88–112.

Hunaiti et al., Antimicrobial Agents and Chemotherapy (1984), 25(2):173–178.

Kao C.M., et al., Science (1994), 265:509–512.

Khosla et al., J. Bacteriol. (1993), 175(8):2197–2204.

Lanz et al., J. of Biol. Chem. (1991), 266(15):9971–9976.

Leadlay et al., Biochem. Soc. Transactions (1993), 21:218–21222.

MacNeil et al., Gene (1992), 115:119–125.

Malpartida et al., Nature (1984), 309:462–464.

Malpartida et al., Mol. Gen. Genet. (1986), 205:66–73.

Marsden et al., Science (1994), 263:378–380.

Omura et al., J. Biochem. (1974), 75:193–195.

Roberts et al., FEBS Lett. (1983), 1591(1,2):13–16.

Roberts et al., Biochem. Soc. Transactions (1984), 12:642–3.

Rudd, et al., J. Gen. Microbiol. (1979), 114:35–43.

Shen et al., Science (1993), 262:1535–40.

Sherman et al., EMBO J. (1989), 8(9):2717–25.

Sherman et al., J. Bacteriol. (1992), 174(19):6184–90.

Spencer et al., Biochem. J. (1992), 288:839–46.

Wawszkiewicz et al., Biochemische Zeitschrift (1964), 340:213–27.

US 6,274,560 B1

CELL-FREE SYNTHESIS OF POLYKETIDES

CROSS-REFERENCE TO RELATED APPLICATION

This application is related to provisional patent application serial no. 60/003,338, filed Jul. 6, 1995, and is a divisional application of patent application Ser. No. 08/675,817, filed Jul. 5, 1996 now U.S. Pat. No. 6,080,555, from which priority is claimed under 35 U.S.C. §119(e)(1) and which are incorporated herein by reference in its entirety.

REFERENCE TO GOVERNMENT CONTRACT

This invention was made with United States Government support in the form of a grant from the National Institutes of Health (GM22172 and CA 66736-01).

TECHNICAL FIELD

The present invention relates generally to polyketides and polyketide synthases. In particular, the invention pertains to novel methods of producing polyketides and libraries of polyketides using a cell-free system.

BACKGROUND OF THE INVENTION

Polyketides are a large, structurally diverse family of natural products. Polyketides possess a broad range of biological activities including antibiotic and pharmacological properties. For example, polyketides are represented by such antibiotics as tetracyclines and erythromycin, anticancer agents including daunomycin, immunosuppressants, for example FK506 and rapamycin, and veterinary products such as monensin and avermectin.

Polyketides occur in most groups of organisms and are especially abundant in a class of mycelial bacteria, the actinomycetes, which produce various polyketides. Polyketide synthases (PKSs) are multifunctional enzymes related to fatty acid synthases (FASs). PKSs catalyze the biosynthesis of polyketides through repeated (decarboxylative) Claisen condensations between acylthioesters, usually acetyl, propionyl, malonyl or methylmalonyl. Following each condensation, they introduce structural variability into the product by catalyzing all, part, or none of a reductive cycle comprising a ketoreduction, dehydration, and enoylreduction on the $\beta$-keto group of the growing polyketide chain. PKSs incorporate enormous structural diversity into their products, in addition to varying the condensation cycle, by controlling the overall chain length, choice of primer and extender units and, particularly in the case of aromatic polyketides, regiospecific cyclizations of the nascent polyketide chain. After the carbon chain has grown to a length characteristic of each specific product, it is released from the synthase by thiolysis or acyltransfer. Thus, PKSs consist of families of enzymes which work together to produce a given polyketide. It is the controlled variation in chain length, choice of chain-building units, and the reductive cycle, genetically programmed into each PKS, that contributes to the variation seen among naturally occurring polyketides.

Two general classes of PKSs exist. These classifications are well known. See, for example, Hopwood, D. A. and Khosla, C., *Secondary Metabolites: Their Function and Evolution* (1992) Wiley Chichester (Ciba Foundation Symposium 171) pp. 88–112.

One class, known as Type I or modular PKSs, is represented by the PKSs which catalyze the biosynthesis of complex polyketides such as erythromycin and avermectin. These "modular" PKSs include assemblies of several large multifunctional proteins carrying, between them, a set of separate active sites for each step of carbon chain assembly and modification (Cortes, J. et al. *Nature* (1990) 348:176; Donadio, S. et al. *Science* (1991) 252:675; MacNeil, D. J. et al. *Gene* (1992) 115:119). The active sites required for one cycle of condensation and reduction are clustered as "modules" (Donadio et al. *Science* (1991), supra; Donadio, S. et al. *Gene* (1992) 111:51). For example, 6-deoxyerythronolide B synthase (DEBS) consists of the three multifunctional proteins, DEBS 1, DEBS 2, and DEBS 3 (Caffrey, P. et al. *FEBS Letters* (1992) 304:225), each of which possesses two modules. (See FIG. 1.)

As described below, a module contains at least the minimal activities required for the condensation of an extender unit onto a growing polyketide chain; the minimal activities required are a ketosynthase (KS), an acyl transferase (AT) and an acyl carrier protein (ACP). Additional activities for further modification reactions such as a reductive cycle or cyclization may also be included in a module. Structural diversity occurs in this class of PKSs from variations in the number and type of active sites in the PKSs. This class of PKSs displays a one-to-one correlation between the number and clustering of active sites in the primary sequence of the PKS and the structure of the polyketide backbone.

The second class of PKSs, the aromatic or Type II PKSs, has a single set of iteratively used active sites (Bibb, M. J. et al. *EMBO J.* (1989) 8:2727; Sherman, D. H. et al. *EMBO J.* (1989) 8:2717; Fernandez-Moreno, M. A. et al. *J. Biol. Chem.* (1992) 267:19278). Streptomyces is an actinomycete which is an abundant producer of aromatic polyketides. In each Streptomyces aromatic PKS so far studied, carbon chain assembly requires the products of three open reading frames (ORFs). (See FIG. 2.) ORF1 encodes a ketosynthase (KS) and an acyltransferase (AT) active site (KS/AT); ORF2 encodes a chain length determining factor (CLF), a protein similar to the ORF1 product but lacking the KS and AT motifs; and ORF3 encodes a discrete acyl carrier protein (ACP). Some gene clusters also code for a ketoreductase (KR) and a cyclase, involved in cyclization of the nascent polyketide backbone. However, it has been found that only the KS/AT, CLF, and ACP, need be present in order to produce an identifiable polyketide.

Fungal PKSs, such as the 6-methylsalicylic acid PKS, consist of a single multidomain polypeptide which includes all the active sites required for the biosynthesis of 6-methylsalicylic acid (Beck, J. et al. *Eur. J. Biochem.* (1990) 192:487–498; Davis, R. et al. *Abstr. of the Genetics of Industrial Microorganism Meeting, Montreal, abstr.* P288 (1994)). Fungal PKSs incorporate features of both modular and aromatic PKSs.

Streptomyces coelicolor produces the blue-pigmented polyketide, actinorhodin. The actinorhodin gene cluster (act), has been cloned (Malpartida, F. and Hopwood, D. A. *Nature* (1984) 309:462; Malpartida, F. and Hopwood, D. A. *Mol. Gen. Genet.* (1986) 205:66) and completely sequenced (Fernandez-Moreno et al. *J. Biol. Chem.* (1992), supra; Hallam, S. E. et al. *Gene* (1988) 74:305; Fernandez-Moreno, M. A. et al. *Cell* (1991) 66:769; Caballero, J. et al. *Mol. Gen. Genet.* (1991) 230:401). The cluster encodes the PKS enzymes described above, a cyclase and a series of tailoring enzymes involved in subsequent modification reactions leading to actinorhodin, as well as proteins involved in export of the antibiotic and at least one protein that specifically activates transcription of the gene cluster. Other genes required for global regulation of antibiotic biosynthesis, as well as for the supply of starter (acetyl-CoA) and extender (malonyl-CoA) units for polyketide biosynthesis, are located elsewhere in the genome.

The act gene cluster from *S. coelicolor* has been used to produce actinorhodin in *S. parvulus*. Malpartida, F. and Hopwood, D. A. *Nature* (1984) 309:462.

Bartel et al. *J. Bacteriol.* (1990) 172:4816–4826, recombinantly produced aloesaponarin II using *S. galilaeus* transformed with an *S. coelicolor* act gene cluster consisting of four genetic loci, acti, actIII, actIV and actVII. Hybrid PKSs, including the basic act gene set but with ACP genes derived from granaticin, oxytetracycline, tetracenomycin and frenolicin PKSS, have also been designed which are able to express functional synthases. Khosla, C. et al. *J. Bacteriol.* (1993) 175:2197–2204. Hopwood, D. A. et al. *Nature* (1985) 314:642–644, describes the production of hybrid aromatic polyketides, using recombinant techniques. Sherman, D. H. et al. *J. Bacteriol.* (1992) 174:6184–6190, reports the transformation of various S. coelicolor mutants, lacking different components of the act PKS gene cluster, with the corresponding granaticin (gra) genes from S. violaceoruber, in trans.

Although the above described model for complex polyketide biosynthesis by modular (Type I) PKSs has been substantiated by radioisotope and stable isotope labeling experiments, heterologous expression, directed mutagenesis, and in vitro studies on partially active proteins, cell-free enzymatic synthesis of complex polyketides has proved unsuccessful despite more than 30 years of intense efforts (Caffrey et al. *FEBS Letters* (1992), supra; Aparicio, J. F. et al. *J. Biol. Chem.* (1994) 269:8524; Bevitt, D. J. et al. *Eur. J. Biochem.* (1992) 204:39; Caffrey, P. et al. *Eur. J. Biochem.* (1991) 195:823); Leadlay, P. F. et al. *Biochem. Soc. Trans.* (1993) 21:218; Marsden, A. F. A. et al. *Science* (1994) 263:378; Wawszkiewicz, E. J. et al. *Biochemische Z.* (1964) 340:213; Corcoran, J. W. et al. in *Proc. 5th Int. Congr. Chemother.* (Vienna, 1967), Abstracts of Communications, p. 35; Corcoran, J. W. et al. in *Antibiotics IV. Biosynthesis* (1982) Corcoran, J. W., Ed. (Springer-Verlag, New York) p. 146; Roberts, G. *FEBS Lett.* (1983) 159:13; Roberts, G. et al. *Biochemical Soc. Trans.* (1984) 12:642; Hunaiti, A. A. et al. *Antimicrob. Agents. Chemother.* (1984) 25:173). This is due, in part, to the difficulty of isolating fully active forms of these large, poorly expressed multifunctional proteins from naturally occurring producer organisms and, in part, to the relative lability of intermediates formed during the course of polyketide biosynthesis. For example, the three DEBS proteins have been purified individually from the natural producer organism, *Saccharopolyspora erythraea* (Caffrey et al. *FEBS Letters* (1992), supra; Aparicio et al. *J. Biol. Chem.* (1994), supra; Bevitt et al. *Eur. J. Biochem.* (1992), supra; Caffrey et al. *Eur. J. Biochem.* (1991), supra; Leadlay et al. *Biochem. Soc. Trans.* (1993); Marsden et al. *Science* (1994), supra). Studies on the purified enzymes facilitated clarification of their stereospecificity, showing that 2S-methylmalonyl-CoA is the extender substrate for all 6 acyltransferase sites (Marsden et al. *Science* (1994), supra), thereby implying that the differing configurations of the methyl-branched centers result from selective epimerization of specific enzyme-bound intermediates. However, the lack of a full turnover assay prevented these investigators from probing the mechanisms of the enzyme complex in greater detail.

In an attempt to overcome some of these limitations, modular PKS subunits have been expressed in heterologous hosts such as *E. coli* (Aparicio et al. *J. Biol. Chem.* (1994), supra; Bevitt et al. *Eur. J. Biochem.* (1992), supra; Caffrey et al. *Eur. J. Biochem.* (1991), supra; Leadlay et al. *Biochem.*
*Soc. Trans.* (1993);) and *S. coelicolor* (Kao, C. M. et al. *Science* (1994) 265:509; International Publication No. WO 95/08548 (published Mar. 30, 1995)). Whereas the proteins expressed in *E. coli* are not fully active, heterologous expression in *S. coelicolor* resulted in production of active protein as demonstrated by the production of 6-deoxyerythronolide ("6-DEB") in vivo. Cell-free enzymatic synthesis of polyketides from simpler PKSs such as the 6-methylsalicylate synthase (Dimroth, P. et al. *Eur. J. Biochem.* (1970) 13:98; Beck, J. et al. *Eur. J. Biochem.* (1990) 192:487); Spencer J. B. et al. *Biochem. J.* (1992) 288:839), chalcone synthase (Lanz, T. et al. *J. Biol. Chem.* (1991) 266:9971 (1991)), and the tetracenomycin synthase (Shen, B. et al. *Science* (1993) 262:1535) has been reported.

However, no one to date has described the cell-free enzymatic synthesis of polyketides from modular PKSs, or has used a cell-free system to produce libraries containing a multiplicity of different polyketides.

SUMMARY OF THE INVENTION

The present invention provides methods to produce both novel and known polyketides. In one embodiment, a cell-free system comprising a modular PKS effects synthesis of a polyketide when incubated with an appropriate substrate set.

In another embodiment, the invention is directed to a method of synthesizing a library containing a multiplicity of different polyketides by use of cell-free systems and to a matrix of cell-free subsystems for the production of these libraries.

Thus, in one aspect, the invention is directed to a method comprising providing one or more proteins comprising at least two modules of a modular polyketide synthase in a cell-free system; adding to said system at least one starter unit and at least one extender unit; incubating said cell-free system containing said starter unit and extender unit under conditions wherein said polyketide is synthesized; and optionally recovering the polyketide from the cell-free system.

In another aspect, the invention is directed to a matrix for the production of a polyketide library which comprises a series of cell-free subsystems each containing one or more polyketide synthase proteins comprising enzymatic activities that effect the coupling of at least one extender unit to a starter unit, including a growing polyketide chain; each said subsystem containing at least one starter unit and at least one extender unit; and wherein at least one enzymatic activity or at least one extender unit or at least one starter unit or is different as between each subsystem.

The invention in another aspect is directed to methods to prepare libraries of polyketides using these matrices.

In yet another aspect, the invention is directed to method to produce a desired polyketide which method comprises: providing a system comprising a functional modular polyketide synthase (PKS), or a functional portion thereof, wherein said PKS cannot be loaded with a natural first-module starter unit, or wherein, once loaded, cannot catalyze the condensation of an extender unit to the first-module starter unit to produce a polyketide intermediate; adding to said system a starter unit that is a substrate for the PKS; incubating the system containing said PKS and said starter unit substrate under conditions wherein said polyketide is synthesized; and optionally recovering the polyketide.

In still another aspect, the invention is directed to a functional modular polyketide synthase system, or a functional portion thereof, which cannot be loaded with a natural first-module starter unit, or which, once loaded, cannot catalyze the condensation of an extender unit to the first-module starter unit to produce a polyketide intermediate.

DETAILED DESCRIPTION OF THE INVENTION

Figure 1:
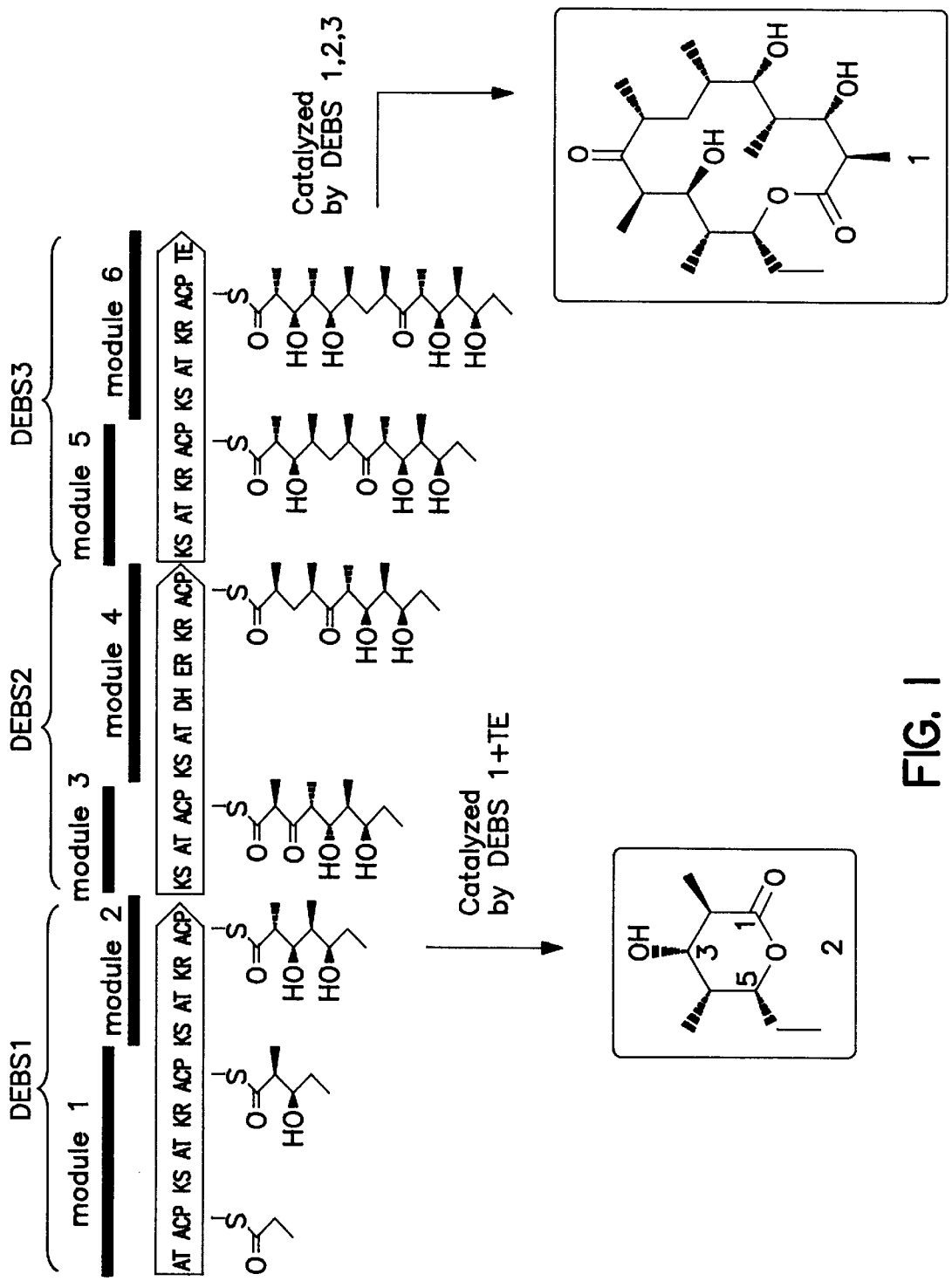
FIG. 1 is a diagram of the organization of the modular PKS cluster which catalyzes the production of 6-DEB (1).
Figure 2:
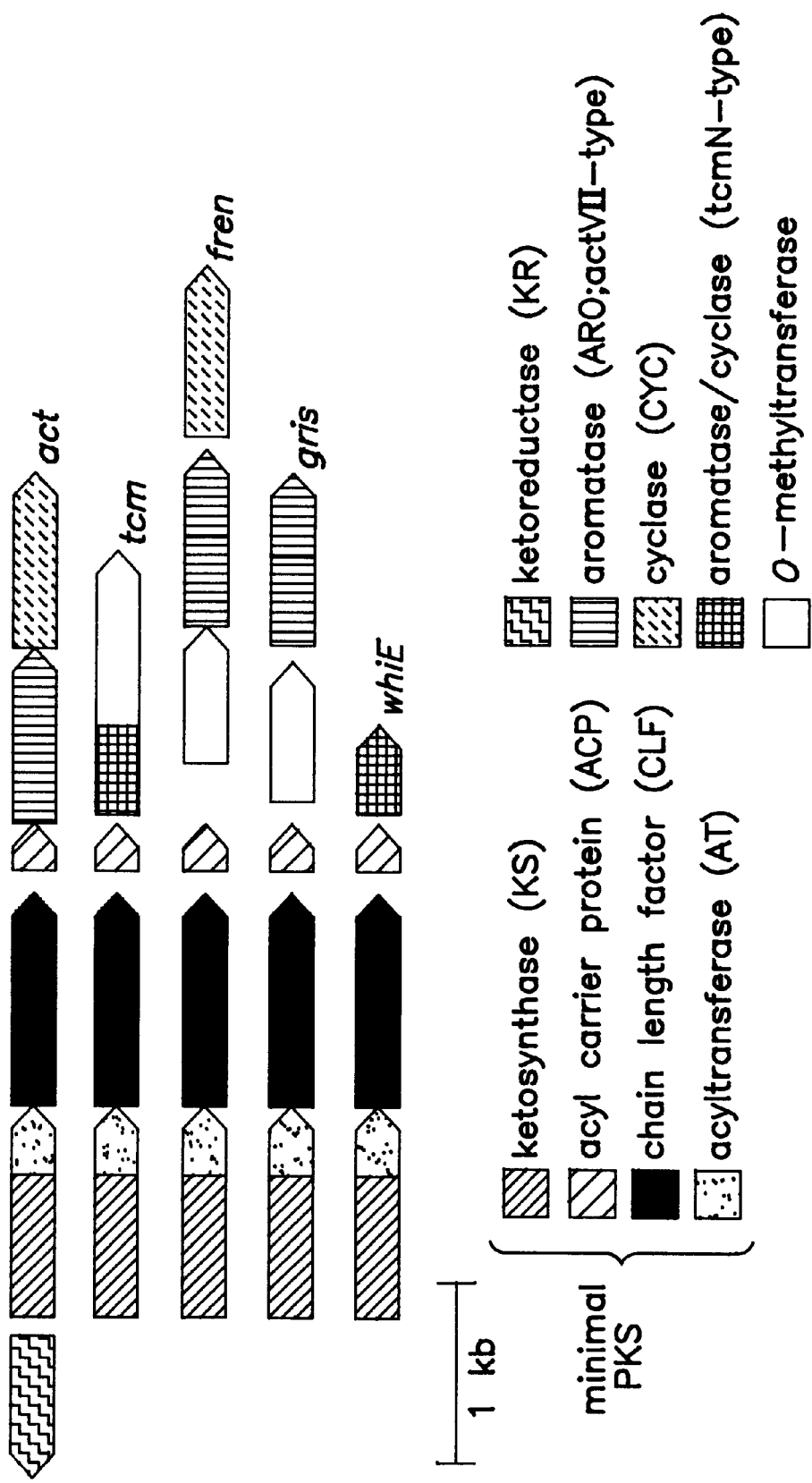
FIG. 2 diagrams a typical aromatic PKS gene cluster.

The invention provides cell-free systems for the synthesis of novel and known polyketides and of polyketide libraries. In the case of modular polyketide synthases, cell-free production of polyketides using these enzymes has not heretofore been accomplished. Although, as described above, cell-free synthesis of polyketides by some aromatic synthases has been achieved, these systems have not been used in constructing libraries of polyketides, said libraries being useful as sources of compounds to be screened for pharmacological or other activities.

The use of cell-free systems for the construction of such libraries has several advantages. First, permeability problems are eliminated, so that substrates can be used which might otherwise be ineffective due to failure to permeate the cell. Second, variability in product due to differential permeability is eliminated. Third, alternative metabolic events are minimized or eliminated so that the reaction proceeds cleanly to convert substrates to polyketide products. Fourth, there are greater possibilities for regulating the conditions under which the polyketide synthase genes are expressed and the polyketides are produced. For example, cofactors which are ordinarily useful in the synthesis of a given polyketide, such as NADPH, can be supplied or withheld. Finally, it is possible to use "unnatural" substrates for a given synthase since cellular mechanisms for providing the substrate to the synthase are eliminated. As a result of using cell-free systems to create libraries, a greater variety of polyketides may be synthesized than would have been possible had production been limited to intracellular synthesis.

Given a particular cell-free system containing polyketide synthase proteins, the nature of the polyketide ultimately produced will depend on the substrates provided and on the conditions with respect to cofactors, etc. In order to explore the possibilities for a given cell-free system with a given complement of PKS proteins, it will be advantageous to subdivide the cell-free system into "subsystems" with variation in these factors. In order to be workable, the cell-free system or subsystem must contain polyketide synthase proteins with enzymatic activities sufficient to effect the condensation of an "extender unit" onto a "starter unit," where a "starter unit" may include a growing polyketide chain. Because the cell-free system offers greater promiscuity of starter and extender units, a number of subsystems containing a variety of starter and extender units, as well as differing conditions may result in a corresponding variety of polyketides.

As used in the present application, a "starter unit" refers to a substance to which additional Claisen condensations may be effected. The starter unit may be one which is natively regarded as a starter, or may be what would in the native state be an intermediate growing polyketide chain. A "first-module starter unit" is an acyl thioester that can be loaded onto the appropriate active site of the first module of a PKS. A "natural starter unit" is an acyl thioester which upon extension by the PKS produces the natural polyketide product. An "unnatural starter unit" is an acy thioester which upon extension by the PKS produces a polyketide product other than that normally produced by the PKS during metabolism.

A relaxed specificity of modular PKS for starter units under in vitro conditions has been reported by Pieper et al. *Nature* (1995) 378:263–266. Known starter units include, for example acetyl-CoA, propionyl-CoA, butyryl-CoA, isobutyryl-CoA, cyclohexanoyl-CoA, aminohydroxy benzoyl-CoA, and intermediate polyketide chains. In addition, an extender unit may be used as a source of starter units (see Pieper et al. *Biochem.* (1996) 35:2054–2060). Thus, in a system capable of producing a polyketide, the starter unit and the extender unit used therein may be the same or different.

The starter unit is then extended by virtue of the activity of the synthase contained in the cell-free system or subsystem. Extender units are added to the carboxy terminus of a growing polyketide and the nature of the extender unit is determined by the acyl transferase (AT) activity. Suitable extender units include malonyl-CoA, methylmalonyl-CoA and ethylmalonyl-CoA. Sequence comparisons have identified the characteristics of malonyl-CoA-specific AT and methylmalonyl-CoA-specific AT (Haydock et al. *FEBS Lett.* (1995) 374:246–248. When methylmalonyl-CoA or ethylmalonyl-CoA is used as the extender unit, a chiral center is generated in the condensation.

The reductive cycle which occurs in either aromatic or modular PKS systems depends both on the presence of suitable ketoreductase (KR) activity as well as the reaction conditions in an in vitro system. The absence of reductive activity yields a ketone; reduction generates an alcohol containing a chiral center. If a dehydratase (DH) activity is also present, an alkene results which eliminates the chiral center. Additionally, an enoyl reductase activity may be present which reduces the β-keto group to a methylene group. Thus, for a single condensation of an extender unit, there are five theoretically possible reductive cycle outcomes. This variation is effected both by the cofactor conditions and by the nature of the proteins in the cell-free system to be employed.

Various other catalytic activities resulting in cyclization, aromatization, chain-length limitation, and the like are determined mainly by the nature of the synthase proteins.

Thus, the availability of cell-free systems for the production of ketides provides a unique opportunity to generate libraries of polyketides by varying the nature of the synthase, the nature of the extender unit, the nature of the starter unit and the nature of the conditions. A simple matrix can be envisioned whereby cell-free systems containing varying synthase catalytic activities, but at a minimum the capability to extend a starter unit, including a growing polyketide chain through an additional Claisen condensation, can be employed. Each of these cell-free systems can be subdivided into subsystems in which the remaining variables are manipulated to effect the eventual outcome of synthesis. Thus, a series of subsystems containing identical polyketide synthase activities can be supplied different starter units, different extender units, and incubated under different conditions so as to result in a multiplicity of polyketides. Similar variation can be employed with respect to subsystems of cell-free systems containing different PKS activities, thus resulting in a matrix wherein one dimension may be envisioned as varying the nature of the cell-free system itself and the other dimension comprises variation in the substrates and conditions.

A. Definitions

In describing the present invention, the following terms will be employed, and are intended to be defined as indicated below.

By a "cell-free system" is intended a cell lysate, cell extract or other preparation in which substantially all of the cells in the preparation have been disrupted or otherwise processed so that all or selected cellular components, e.g., organelles, proteins, nucleic acids, the cell membrane itself (or fragments or components thereof), or the like, are released from the cell or resuspended into an appropriate medium and/or purified from the cellular milieu. Cell-free systems include, of course, reaction mixtures prepared from purified or isolated proteins and suitable reagents and buffers.

By a "cell-free subsystem" is meant either a portion of a cell-free system—i.e., the cell-free system that results when a given composition is effectively subdivided into two or more separate compartments for independent catalysis, or is a reaction mixture which contains the same complement of polyketide synthase enzymatic activity. Thus, a "subsystem" of a given "cell-free system" may differ in composition by virtue of differing substrates or conditions, but contains the same catalytic polyketide synthase activities.

By "purified" or "isolated" is meant, when referring to a polypeptide or nucleotide sequence, that the indicated molecule is separate and discrete from the whole organism from which the molecule is normally associated in nature. Thus, a protein contained in a cell free extract would constitute a "purified" or "isolated" protein, as would a protein further purified from a cell-free extract. In addition, a "purified" or "isolated" protein refers to a protein which has been synthetically or recombinantly produced and, optionally, purified from the host cell. An "isolated" nucleotide sequence is a nucleotide sequence separate and discrete from the whole organism with which the sequence is found in nature; or a sequence devoid, in whole or part, of sequences normally associated with it in nature; or a sequence, as it exists in nature, but having heterologous sequences (as defined below) in association therewith.

A single "module" of a modular PKS gene cluster or a modular polyketide synthase refers to sufficient portions of the gene cluster to encode, or sufficient portions of the polyketide synthase to include, at least the activities required to effect the condensation of a single extender unit onto a starter unit or a growing polyketide chain. Thus, the minimal activities required include a ketosynthase (KS) an acyltransferase (AT) and an acyl carrier protein (ACP). All three of these activities are required for the condensation of a single extender unit onto the growing polyketide chain. At least one module for the effective synthesis of a polyketide must contain an additional AT and ACP in order to effect the initial condensation. In addition, and optionally, the module may include a ketoreductase activity (KR), a cyclase, a dehydratase (DH) an enoyl reductase (ER) and/or a thioesterase (TE).

In native forms of aromatic polyketide synthases, portions of the required activities may occur on different proteins. In the case of aromatic polyketide synthases also, a ketosynthase (KS), an acyl transferase (AT) and an acyl carrier protein (ACP) must be present to effect the condensation of a single extender unit onto a starter unit or a growing polyketide. Various activities associated with reduction, cyclization, aromatization and further derivatization may also be present. There must also be at least one chain-length limiting factor (CLF).

The phrases "IPKS gene cluster" and "PKS gene set" are used interchangeably to mean any set of PKS genes capable of producing a functional PKS when under the direction of one or more compatible control elements, as defined below, in a host cell. A functional PKS is one which catalyzes the condensation of at least one extender unit onto a growing polyketide—i.e., has at least one functional module, or extension function either in vivo or in vitro. A "PKS gene cluster" thus need not include all of the genes found in the corresponding cluster in nature.

Furthermore, the cluster can include PKS genes derived from a single species, or may be hybrid in nature with, e.g., a coding sequence derived from a cluster for the synthesis of a particular polyketide replaced with a corresponding coding sequence from a cluster for the synthesis of another polyketide. Hybrid clusters can include genes derived from either or both modular and aromatic PXSs. The genes included in the gene cluster need not be the native genes, but can be mutants or analogs thereof. Mutants or analogs may be prepared by the deletion, insertion or substitution of one or more nucleotides of the coding sequence. Techniques for modifying nucleotide sequences, such as site-directed mutagenesis, are described in, e.g., Sambrook et al., supra; *DNA Cloning,* Vols. I and II, supra; *Nucleic Acid Hybridization,* supra.

A "PKS gene cluster" may also contain genes coding for modifications to the core polyketide produced by the PKS, including, for example, genes encoding post-polyketide synthesis enzymes derived from natural products pathways such as O-methyltransferases and glycosyltransferases. A "PKS gene cluster" may further include genes encoding hydroxylases, methylases or other alkylases, oxidases, reductases, glycotransferases, lyases, ester or amide synthases, and various hydrolases such as esterases and amidases.

As explained further below, the genes included in the PKS gene cluster need not be on the same plasmid or, if present on the same plasmid, can be controlled by the same or different control sequences.

A "host cell" is a cell and the progeny and cultures thereof derived from a procaryotic microorganism or a eucaryotic cell line cultured as a unicellular entity, which can be, or has been, used as a recipient for recombinant vectors bearing the PKS gene clusters of the invention. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired PKS, are included in the definition, and are covered by the above terms.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention. Allelic variation or naturally occurring mutational events do not give rise to heterologous DNA, as used herein.

A "coding sequence" or a sequence which "encodes" a protein or peptide is a nucleic acid sequence which is transcribed into mRNA (in the case of DNA) or translated into a polypeptide (in the case of mRNA) in vitro or in vivo when placed under the control of appropriate regulatory sequences. "Control sequences" refers collectively to promoter sequences, ribosome binding sites, polyadenylation signals, transcription termination sequences, upstream regulatory domains, enhancers, and the like, which collectively provide for the transcription and/or translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "library" or "combinatorial library" of polyketides is intended to mean a collection of a multiplicity of different polyketides. The differences in the members of the library may result from their being produced by different PKS cell-free systems that contain any combination of native, homolog or mutant genes from aromatic, modular or fungal PKSs. The differences in the members of the library may also result from the use of different starter units, extender units and conditions. The PKSs in the cell-free systems used to generate the library may be derived from a single system, such as act, fren, gra, tcm, whiE, gris, ery, or the like, and may optionally include genes encoding tailoring enzymes which are capable of catalyzing the further modification of a polyketide. Alternatively, the combination of synthase activities can be rationally or stochastically derived from an assortment of synthases, e.g., a synthase system can be constructed to contain the KS/AT component from an act PKS, the CLF component from a gra PKS and a ACP component from a fren PKS. The synthase can optionally include other enzymatic activities as well.

The variety of polyketides in the library may thus result from varying the nature of the synthase or varying the nature of the substrates used to construct the polyketides or both. Preferably, the library is produced as a result of culturing a matrix which varies the nature of the synthase systems in one dimension and the nature of the substrates and/or incubation conditions in the other. The library of polyketides thus produced can be tested or screened for biological, pharmacological or other activity.

"Optional" or "optionally" means that the subsequently described event or circumstance may or may not occur, and that the description includes instances where said event or circumstance occurs and instances where it does not. For example, the phrase "optionally further purified" means that further purification may or may not be performed and that the description includes both the performance and the lack of performance of such further purification.

B. General Methods

The polyketides produced by the invention methods can be screened for use as therapeutic agents to treat a number of disorders, depending on the type of polyketide in question. For example, several of the polyketides produced by the present method will find use as immunosuppressants, as anti-tumor agents, as well as for the treatment of viral, bacterial and parasitic infections.

By use of the cell-free systems of the invention, a wide variety of polyketides can be synthesized as candidates. As explained above, the use of cell-free technology permits greater flexibility in choice of substrate and less interference in the synthesis of the desired polyketide from competing metabolic reactions. The ability to produce polyketides in a cell-free system also provides a powerful tool for characterizing PKSs and the mechanism of their actions.

The practice of the present invention will employ, unless otherwise indicated, conventional methods of chemistry, microbiology, molecular biology and recombinant DNA techniques within the skill of the art. Such techniques are explained fully in the literature. See, e.g., Sambrook, et al. *Molecular Cloning: A, Laboratory Manual* (Current Edition); *DNA Cloning: A Practical Approach,* vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); H. O. House, *Modern Synthetic Reactions,* Second Edition (Menlo Park, Calif.: The Benjamin/Cummings Publishing Company, 1972); and J. March, *Advanced organic Chemistry: Reactions, Mechanisms and Structure*, 4th Ed. (New York:

Wiley-Interscience, 1992).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, reference to "a polyketide synthase" includes mixtures of polyketide synthases, reference to "a PKS enzyme" includes mixtures of such enzymes, and the like.

1. Recombinant Production of PKS

The invention, for the production and isolation of a significant quantity of functional modular PKS enzymes, in particular, makes use of host cells transformed with recombinant vectors for the production of these enzymes. Aromatic and hybrid PKS may be produced in this way as well. The host cells may be genetically engineered cells which have their naturally occurring PKS genes substantially deleted.

Host cells for the production of the functional PKS enzymes effective in cell-free systems can be derived from any organism with the capability of harboring a recombinant PKS gene cluster, and can be derived from either procaryotic or eucaryotic organisms. However, preferred host cells are those constructed from the actinomycetes, a class of mycelial bacteria which are abundant producers of a number of polyketides. A particularly preferred genus for use in production of the PKSs is Streptomyces. Thus, for example, *S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber*, among others, will provide convenient host cells, with *S. coelicolor* being preferred. (See, e.g., Hopwood, D. A. and Sherman, D. H. *Ann. Rev. Genet.* (1990) 24:37–66; O'Hagan, D. *The Polyketide Metabolites* (Ellis Horwood Limited, 1991), for a description of various polyketide-producing organisms and their natural products.)

The above-described cells can be genetically engineered by deleting the naturally occurring PKS genes therefrom, using standard techniques, such as by homologous recombination. (See, e.g., Khosla, C. et al. *Molec. Microbiol.* (1992) 6:3237). For example, native strains of *S. coelicolor* produce a PKS which catalyzes the biosynthesis of the aromatic polyketide actinorhodin. The strain, *S. coelicolor* CH999 (as described in WO 95/08548, supra), was constructed by deleting, via homologous recombination, the entire natural act cluster from the chromosome of *S. coelicolor* CH1 (Khosla et al. *Molec. Microbiol.* (1992), supra), a strain lacking endogenous plasmids and carrying a stable mutation that blocks biosynthesis of another pigmented *S. coelicolor* antibiotic, undecylprodigiosin.

The host cells described above can be transformed with one or more vectors, collectively encoding at least a set of functional PKS activities sufficient to effect condensation of an extender unit, or a cocktail comprising a random assortment of PKS associated sequences with this activity. The vector(s) can include native or hybrid combinations of PKS subunits or cocktail components, or mutants thereof.

In order to produce the PKS for practice of the cell-free synthesis, recombinant vector(s) can be constructed that include genes from a single PKS aromatic or modular gene cluster, or may comprise hybrid PKS gene clusters with, e.g., a gene or part of a gene from one cluster replaced by the corresponding portion from another gene cluster. For example, it has been found that ACPs are readily interchangeable among different aromatic synthases without an effect on product structure. Furthermore, a given KR can recognize and reduce polyketide chains of different chain lengths. Accordingly, these coding sequences are freely interchangeable in the constructs described herein. Thus, the PKS gene clusters used to produce the PKS enzymes can be derived from any combination of PKS gene sequences which ultimately function to produce a PKS that condenses at least one extender unit into a growing polyketide.

Examples of hybrid clusters include clusters with coding sequences derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. A number of hybrid gene clusters have been constructed having components derived from the act, fren, tcm, gris and gra gene clusters (see, WO 95/08548). Several of the hybrid clusters were able to functionally express both novel and known polyketides in *S. coelicolor* CH999. However, other hybrid gene clusters, as described above, can easily be produced and screened using the disclosure herein, for the production of identifiable polyketides.

The recombinant vectors, harboring the gene clusters or random assortment of PKS genes, modules, active sites or portions thereof described above, can be conveniently generated using techniques known in the art. For example, the PKS subunits of interest can be obtained from an organism that expresses the same, using recombinant methods, such as by screening cDNA or genomic libraries, derived from cells expressing the gene, or by deriving the gene from a vector known to include the same. The gene can then be isolated and combined with other desired PKS subunits, using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Mutations can be made to the native PKS subunit sequences and such mutants used in place of the native sequence, so long as the mutants are able to function with other PKS subunits to collectively catalyze the synthesis of an identifiable polyketide. Such mutations can be made to the native sequences using conventional techniques such as by preparing synthetic oligonucleotides including the mutations and inserting the mutated sequence into the gene encoding a PKS subunit using restriction endonuclease digestion. (See, e.g., Kunkel, T. A. (1985) *Proc. Natl. Acad. Sci. USA* 82:448; Geisselsoder et al. (1987) *BioTechniques* 5:786.) Alternatively, the mutations can be effected using a mismatched primer (generally 10–20 nucleotides in length) which hybridizes to the native nucleotide sequence (generally CDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409. PCR mutagenesis will also find use for effecting the desired mutations.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis" as described in U.S. Pat. No. 5,521,077 to Khosla et al.

The gene sequences, native or mutant, which collectively encode PKS protein(s) at least sufficient to catalyze condensation of an extender unit, can be inserted into one or more expression vectors, using methods known to those of skill in the art. In order to incorporate a random assortment of PKS genes, modules, active sites or portions thereof into am expression vector, a cocktail of same can be prepared and used to generate the expression vector by techniques well known in the art and described in detail below. Expression vectors will include control sequences operably linked to the desired PKS coding sequence. Suitable expression systems for use with the present invention include systems which function in eucaryotic and procaryotic host cells. However, as explained above, procaryotic systems are preferred, and in particular, systems compatible with Streptomyces spp. are of particular interest. Control elements for use in such systems include promoters, optionally containing operator sequences, and ribosome binding sites. Particularly useful promoters include control sequences derived from PKS gene clusters which result in the production of functional PKS enzymes, such as one or more act promoters, tcm promoters, spiramycin promoters, and the like. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the β-lactamase (bla) promoter system, bacteriophage lambda PL, and T5. In addition, synthetic promoters, such as the tac promoter (U.S. Pat. No. 4,551,433), which do not occur in nature also function in bacterial host cells.

Other regulatory sequences may also be desirable which allow for regulation of expression of the PKS genes relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for selecting cells successfully transformed by the present constructs, i.e., that express a functional PKS that can be isolated and used to catalytically prepare polyketides in a cell-free system.

The various PKS subunits of interest, or the cocktail of PKS genes, modules, active sites, or portions thereof, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

Using these techniques plasmid pRM5 was constructed as a shuttle vector for the production of the PKS enzymes for use in a cell-free system described herein. Plasmid pRM5 includes the genes encoding the actinorhodin PKS subunits flanked by PacI and NsiI restriction sites. A new nucleotide sequence encoding a PKS flanked by PacI and NsiI sites can be easily substituted for the actinrhodin PKS genes. The shuttle plasmid also contains the act KR gene (actIII), the cyclase gene (actVII), and a putative dehydratase gene (actIV), as well as a ColEI replicon (to allow transformation of *E. coli*), an appropriately truncated SCP2* (low copy number) Streptomyces replicon, and the actII-ORF4 activator gene from the act cluster, which induces transcription from act promoters during the transition from growth phase to stationary phase in the vegetative mycelium. pRM5 carries the divergent actI/actIII promoter pair.

Methods for introducing the recombinant vectors of the present invention into suitable hosts are known to those of skill in the art and typically include the use of $CaC_2$ or other agents, such as divalent cations and DMSO. DNA can also be introduced into bacterial cells by electroporation.

The cells modified to contain expression systems for functional PKS proteins are then cultured under conditions wherein these proteins are produced.

2. Preparation of the Cell-Free System

If the polyketide synthase proteins for use in the cell-free system are to be prepared recombinantly as described above, the cells producing the relevant PKS proteins are optionally harvested and disrupted if the desired proteins have been intracellularly produced. However, if the expression system secretes the protein into growth media, the protein can be purified directly from the media.

If the protein is not secreted, it can be isolated from cell lysates. This is generally accomplished by first preparing a crude extract which lacks cellular components and several extraneous proteins. The desired proteins can then be further purified i.e. by column chromatography, HPLC, immunoadsorbent techniques or other conventional methods well known in the art. The selection of the appropriate growth conditions and recovery methods are within the skill of the art.

For example, cells that express the PKS of interest can be grown to produce a predetermined number of cells. The cells may be disrupted by sonication, freeze-thaw cycles or other like techniques by which the cell membrane is breached to form a crude cell-free preparation. The crude cell-free preparation may be used at this stage as a source of PKS or may be further processed by centrifugation, filtration or the like, to form a cell supernatant. Optionally, nucleic acids may be removed from the cell supernatant by, for example, precipitation with polyethyleneimine, or other like agent which does not disturb the enzymatic activity of the PKS. The preparation may be used at this stage as a source of PKS. Optionally, the PKS may be further purified by techniques known to those of skill in the art.

For use in the construction of libraries of polyketides, in addition to recombinantly produced polyketide synthase proteins, isolated native forms may in some instances be used.

The purified PKS can be used to catalytically synthesize polyketides in a cell-free system as exemplified below. The cell-free system includes purified PKS, in an appropriate buffer, and the substrates required for the catalytic synthesis of polyketides. Depending on the PKS, starter substrate units can include, e.g., acetyl-CoA, malonamyl-CoA, propionyl-CoA, butyryl-CoA, isobutyryl-CoA, isovaleryl-CoA, aromatic coenzyme A thioesters such as benzoyl-CoA, aminobenzoyl-CoA, aminohydroxy benzoyl-CoA, and the like, heterocyclics such as thiophenecarboxyl-CoA, and the like, and partially synthesized polyketides. Alternatively, the coenzyme A thioesters may be replaced by corresponding N-acetylcysteamine thioesters. Extender units include, for example, malonyl-CoA, methylmalonyl-CoA, ethylmalonyl-CoA, and other like molecules well known to those of skill in the art.

It has not been possible, heretofore, to provide cell-free systems for the synthesis of polyketides using isolated or purified modular polyketide synthases. According to the present invention, such cell-free systems are provided even for the production of polyketides produced by these complex synthases.

The polyketides that are prepared using the cell-free system disclosed herein may be isolated and identified using any of a variety of techniques known in the art (see, e.g., WO 95/08548) including thin layer chromatography, high performance liquid chromatography, analytical and/or preparative gel electrophoresis, column chromatography, gas chromatography, nuclear magnetic resonance ("NMR"), mass spectrometry, or other conventional methods well known in the art.

3. Additional Background Information on PKS and Use in Library Design

The cell-free preparations described above are particularly useful in constructing polyketide libraries that contain a multiplicity of different polyketides. It will be useful to review the variations that can be included by virtue of varying the proteins containing the PKS catalytic activities required for synthesis. Although hybrid systems can be obtained which combine coding sequences derived from aromatic and modular and fungal PKS, it may be helpful to describe in more detail the mode of action of these PKSs and the combinatorial possibilities. For ease of explanation, the aromatic, modular and fungal PKS systems are discussed separately.

Generally, polyketide synthesis occurs in three stages. In the first stage, catalyzed by the PKS, a nascent polyketide backbone is generated from monomeric CoA thioesters. In the second stage this backbone is regiospecifically cyclized. While some cyclization reactions are controlled by the PKS itself, others result from activities of downstream enzymes. In the final stage, the cyclized intermediate is modified further by the action of mechanistically diverse "tailoring enzymes," giving rise to the natural product.

a) Aromatic PKS

Background:

For aromatic PKS, polyketide biosynthesis begins with a primer unit loading on to the active site of the condensing enzyme, $\beta$-keto acyl synthase/acyl transferase (KS/AT). An extender unit (usually malonate) is then transferred to the pantetheinyl arm of the acyl carrier protein (ACP). The KS/AT catalyzes the condensation between the ACP-bound malonate and the starter unit. Additional extender units are added sequentially until the nascent polyketide chain has grown to a desired chain length determined by the protein chain length factor (CLF), perhaps together with the KS/AT. Thus, the KS, CLF and the ACP form a minimal set to generate a polyketide backbone. The nascent polyketide chain is then subjected to regiospecific ketoreduction by a ketoreductase (KR) if it exists. Cyclases (CYC) and aromatases (ARO) later catalyze regiospecific ring formation events through intramolecular aldol condensations. The cyclized intermediate may then undergo additional regiospecific and/or stereospecific modifications (e.g., O-methylation, hydroxylation, glycosylation, etc.) controlled by downstream tailoring enzymes).

Acetyl-CoA is the usual starter unit for most aromatic polyketides. However, malonamyl-CoA (Gatenbeck, S. *Biochem. Biophy. Res. Commun.* (1961) 6:422–426) and propionyl-CoA (Paulick, R. C. et al. *J. Am. Chem. Soc.* (1976) 98:3370-3371) are primers for many members of the tetracycline and anthracycline classes of polyketides, respectively. Daunorubicin PKS can also accept acetyl-CoA, butyryl-CoA, and isobutyryl-CoA as starter units. (Oki, T. et al. *J. Antibiot.* (1981) 34:783–790; Yoshimoto, A. et al. *J. Antibiot.* (1993) 46:1758–1761).

The act KR can productively interact with all minimal PKSs studied thus far and is both necessary and sufficient to catalyze a C-9 ketoreduction. Although homologous KRs have been found in other PKS clusters, they catalyze ketoreduction with the same regiospecificity. However, the structures of frenolicin, griseusin and daunorubicin suggest that an additional C-17 ketoreduction occurs in these biosynthetic pathways. Likewise, several angucyclines undergo a C-15 ketoreduction, which occurs before the nascent polyketide chain is cyclized (Gould, S. J. et al. *J. Am. Chem. Soc.* (1992) 114:10066–10068). The ketoreductases responsible for C-15 and C-17 reductions have not yet been identified; however, two homologous KRs have been found in the daunorubicin PKS cluster (Grimm, A. et al. *Gene* (1994) 151:1–10; Ye, J. et al. *J. Bacteriol.* (1994) 176:6270–6280). It is likely that they catalyze the C-9 nd C-17 reductions.

The formation of the first two six-membered rings in the biosynthesis of most naturally occurring bacterial aromatic polyketides is controlled by PKS subunits; further ring closures are controlled by additional cyclases and modifying enzymes. The structural diversity introduced via these reactions appears to be greater than via the first two cyclizations. However, certain preferred patterns are observed, which suggests that at least some of these downstream cyclases may be useful for the construction of combinatorial libraries. For example, the pyran ring in isochromanequinones is invariably formed via cyclization between C-3 and C-15; two stereochemically distinct classes of products are observed. In anthracyclines and tetracyclines a third aldol condensation usually occurs between C-3 and C-16, whereas in unreduced tetracenomycins and related compounds it occurs between C-5 and C-18, and in angucyclines it occurs between C-4 and C-17. Representative gene(s) encoding a few of these enzymes have already been cloned (Fernandez-Moreno, M. A. et al. *J. Biol. Chem.* (1994) 269:24854–24863; Shen, B. et al. *Biochemistry* (1993) 32:11149–11154). At least some cyclases might recognize chains of altered lengths and/or degrees of reduction, thereby increasing the diversity of aromatic polyketide combinatorial libraries.

In the absence of downstream cyclases, polyketide chains undergo non-enzymatic reactions.

Recently, some degree of predictability has emerged within this repertoire of possibilities. For instance, hemiketals and benzene rings are two common moieties seen on the methyl end. Hemiketals are formed with an appropriately positioned enol and can be followed by a dehydration. Benzene rings are formed with longer uncyclized methyl terminus. On the carboxyl terminus, a γ-pyrone ring formed by three ketide units is frequently observed. Spontaneous decarboxylations occur on free carboxyl ends activated by the existence of a β-carbonyl.

A cyclized intermediate can undergo various types of modifications to generate the final natural product. The recurrence of certain structural motifs among naturally occurring aromatic polyketides suggests that some tailoring enzymes, particularly group transferases, may be combinatorially useful. Two examples are discussed below.

O-methylation is a common downstream modification. Although several SAM-dependent O-methyltransferase genes have been found in PKS gene clusters (Decker, H. et al. *J. Bacteriol.* (1993) 175:3876–3886), their specificities have not been systematically studied as yet. Perhaps some of them could be useful for combinatorial biosynthesis. For instance, O-11-methylation occurs in several members of the anthracycline, tetracenomycin, and angucycline classes of aromatic polyketides.

Library Design: The following set of design rules permits rationally or stochastically manipulating early biosynthetic steps in aromatic polyketide pathways including chain synthesis, C-9 ketoreduction, ard the formation of the first two aromatic rings. If each biosynthetic degree of freedom is independent of all others, then it should be possible to design a single combinatorial library of $N_1 \times N_2 \times \ldots N_i \times \ldots N_{n-1} \times N_n$ clones, where $N_i$ is the number of ways in which the ith degree of freedom can be exploited. In practice however, not all enzymatic degrees of freedom are independent. Therefore, to minimize redundancy, it is preferable to design several sub-libraries of PKS enzyme-producing clones.

(1) Chain length. In the aromatic synthases, polyketide carbon chain length is dictated by the minimal PKS. Within the minimal PKS, the acyl carrier protein can be interchanged without affecting specificity, whereas the chain length factor is crucial. Although some ketosynthase/chain length factor combinations are functional, others are not; therefore, biosynthesis of a polyketide chain of specified length can be insured with a minimal PKS in which both the ketosynthase and chain length factor originate from the same PKS gene cluster. So far, chain lengths of 16 (octaketide), 18 (nonaketide), 20 (decaketide), and 24 carbons (dodecaketide) can be generated with minimal PKSs from the act, fren, tcm, and, whiE PKS clusters, respectively (McDaniel et al. *Science* (1993), supra; McDaniel et al. *J. Am. Chem. Soc.* (1993), supra; McDaniel et al. *Proc. Natl. Acad. Sci. USA* (1994), supra). The whiE minimal PKS can also generate 22-carbon backbones in the presence of a KR, suggesting a degree of relaxed chain length control as found for the fren PKS.

(2) Ketoreduction. Ketoreduction requires a ketoreductase. The act KR can catalyze reduction of the C-9 carbonyl (counting from the carboxyl end) of a nascent polyketide backbone of any length studied so far.

Furthermore, the act KR is compatible with all the minimal PKSs mentioned above. Homologous ketoreductases have been identified in other PKS clusters (Sherman, D. H., et al. *EMBO J.* (1989) 8:2717–2725; Yu, T. -W. et al. *J. Bacteriol.* (1994) 176:2627–2534; Bibb, M. J. et al. *Gene* (1994) 142:31–39). These enzymes may catalyze ketoreduction at C-9 as well since all the corresponding natural products undergo this modification. In unusual circumstances, C-7 ketoreductions have also been observed with the act KR.

(3) Cyclization of the first ring. Although the minimal PKS alone can control formation of the first ring, the regiospecific course of this reaction may be influenced by other PKS proteins. For example, most minimal PKSs studied so far produce polyketides with C-7/C-12 cyclizations when present alone. In contrast, the tcm minimal PKS alone generates both C-7/C-12 and C-9/C-14 cyclized products. The presence of a ketoreductase with any minimal PKS restricts the nascent polyketide chain to cyclize exclusively with respect to the position of ketoreduction: C-7/C-12 cyclization for C-9 ketoreduction and C-5/C-10 cyclization for C-7 ketoreduction (McDaniel, R. et al. *J. Am. Chem. Soc.* (1993) 115:11671–11675; McDaniel, R. et al. *Proc. Natl., Acad. Sci. USA* (1994) 91:11542–11546; McDaniel, R. et al. *J. Am. Chem. Soc.* (1994) 116:1085510859). Likewise, use of the TcmN enzyme alters the regiospecificity to C-9/C-14 cyclizations for unreduced polyketides of different lengths, but has no effect on reduced molecules.

(4) First ring aromatization. The first ring in unreduced polyketides aromatizes non-catalytically. In contrast, an aromatizing subunit is required for reduced polyketides. There appears to be a hierarchy in the chain length specificity of these subunits from different PKS clusters. For example, the act ARO will recognize only 16-carbon chains (McDaniel et al. *Proc. Natl. Acad. Sci. USA* (1994), supra), the fren ARO recognizes both 16- and 18-carbon chains, while the gris ARO recognizes chains of 16, 18, and 20 carbons.

(5) Second ring cyclization. C-5/C-14 cyclization of the second ring of reduced polyketides may be achieved with an appropriate cyclase. While the act CYC can cyclize octa- and nonaketides, it does not recognize longer chains. No equivalent C-5/C-14 cyclase with specificity for decaketides or longer chains has been identified, although the structures of natural products such as griseusin imply their existence. In the case of sufficiently long unreduced chains with a C-9/C-14 first ring, formation of a C-7/C-16 second ring is catalyzed by the minimal PKS (McDaniel et al. *Proc. Natl. Acad. Sci. USA* (1994), supra).

(6) Additional cyclizations. The KS/AT, CLF, ACP, KR, ARO, and CYC subunits of the PKS together catalyze the formation of an intermediate with a defined chain length, reduction pattern, and first two cyclizations. While the biosynthesis of naturally occurring polyketides typically requires the activity of downstream cyclases and other modifying enzymes to generate the characteristic biologically active product, subsequent reactions in the biosynthesis of engineered polyketides described here and in our earlier work occur in the absence of specific enzymes and are determined by the different physical and chemical properties of the individual molecules. Presumably reflecting such chemical possibilities and constraints, consistent patterns have been observed, leading to some degree of predictability. Two common moieties formed by the uncyclized methyl terminus of polyketide chains are hemiketals and benzene rings. Formation of a hemiketal occurs in the presence of an appropriately positioned enol and can be followed by a dehydration since both the hydrated and dehydrated forms are often isolated (McDaniel, R. et al. *Science* (1993) 262:15461550; McDaniel, R. et al. *J. Am. Chem. Soc.* (1994) 116:1085510859; Fu, H. et al. *J. Am. Chem. Soc.* (1994) 116:41664170), while benzene ring formation occurs with longer unprocessed methyl ends (Fu et al. *J. Am. Chem. Soc.* (1994), supra). The most frequently observed moiety at the carboxyl terminus of the chain is a γ-pyrone ring formed by three ketide units (McDaniel et al. *J. Am. Chem. Soc.* (1994), supra; Fu et al. *J. Am. Chem. Soc.* (1994), supra; Fu, H., et al. *Biochemistry* (1994) 33:9321–9326; Fu, H. et al. *Chem. & Biol.* (1994) 1:205–210; Zhang, H. -I. et al. *J. Org. Chem.* (1990) 55:1682–1684); if a free carboxylic acid remains, decarboxylation typically occurs if a []-carbonyl exists (McDaniel et al. *Science* (1993), supra; McDaniel, R., Ebert-Khosla, S., Hopwood, D. A. & Khosla, C. *J. Am. Chem. Soc.* (1993), supra; Kao, C.M. et al. *J. Am. Chem. Soc.* (1994) 116:11612–11613). Many aldol condensations can be predicted as well, bearing in mind that the methyl and carboxyl ends tend preferentially to cyclize independently but will co-cyclize if no alternative exists (McDaniel et al. *Proc. Natl. Acad. Sci. USA* (1994), supra. These non-enzymatic cyclization patterns observed in vivo are also consistent with earlier biomimetic studies (Griffin, D. A. et al. *J. Chem. Soc. Perkin Trans.* (1984) 1:1035–1042).

Taken together with the structures of other naturally occurring bacterial aromatic polyketides, the design rules presented above can be extrapolated to estimate the extent of molecular diversity that might be generated via in vivo combinatorial biosynthesis of, for example, reduced and unreduced polyketides. For reduced polyketides, the identified degrees of freedom include chain length, aromatization of the first ring, and cyclization of the second ring. For unreduced ones, these include chain length and regiospecificity of the first ring cyclization. The number of accessible structures is the product of the number of ways in which each degree of freedom can be varied. Chains of five different lengths have so far been manipulated (16-, 18- 20-, 22- and 24-carbon lengths). From the structure and deduced biosynthetic pathways of the dynemicin anthraquinone (Tokiwa, Y. et al. *J. Am. Chem. Soc.* (1992) 114:4107–4110), simaomicin (Carter, G. T. et al. *J. org. Chem.* (1989) 54:4321–4323), and benastatin (Aoyama, T. et al. *J. Antibiot.* (1992) 45:1767–1772), the isolation of minimal PKSs that generate 14-, 26-, and possibly 28-carbon backbones, respectively, is anticipated, bringing the potential number to eight. Cloning of such minimal PKSs can be accomplished using the genes for minimal PKSs which have previously been isolated, such as the actI genes (Sherman et al. *EMBO J.* (1989), supra; Yu et al. *J. Bacteriol.* (1994), supra; Bibb et al. *Gene* (1994), supra; Malpartida, F. et al. *Nature* (1987) 325:818–821). Reduced chains can either be aromatized or not; a second ring cyclase is optional where the first ring is aromatized. The regiospecificity of the first cyclization of an unreduced chain can be varied, depending on the presence of an enzyme like TcmN.

For example, for reduced polyketides the relevant degrees of freedom include the chain length (which can be manipulated in at least seven ways), the first ring aromatization (which can be manipulated in at least two ways), and the second ring cyclization (which can be manipulated in at least two ways for aromatized intermediates only). For unreduced polyketides, the regiospecificity of the first cyclization can also be manipulated. Thus, the combinatorial potential for reduced polyketides is at least $7 \times 3 = 21$; for unreduced polyketides the combinatorial potential is at least $7 \times 2 = 14$. Moreover, these numbers do not include additional minor products, on the order of 5 to 10 per major product, that are produced in the recombinant strains through non-enzymatic or non-specific enzyme catalyzed steps. Thus, the number of polyketides that can be generated from combinatorial manipulation of only the first few steps in aromatic polyketide biosynthesis is on the order of a few hundred. Thus, genetically engineered biosynthesis represents a potentially unlimited source of chemical diversity for drug discovery.

b) Modular PKS

Background:

As illustrative of synthesis by modular PKS, polyketide biosynthesis by DEBS begins with the first acyltransferase (AT) activity in module 1 loading the starter unit onto the module 1 condensing activity, the 0-ketoacylsynthase (KS). The second AT of module 1 loads the first extender unit onto the pantetheinyl arm of the acyl-carrier protein (ACP) activity. The KS catalyzes the decarboxylative condensation between the ACP-bound malonyl unit and the primer unit. The resulting diketide is then reduced by the ketoreductase (KR) activity of module 1, which converts the β-keto group into an alcohol. In more complex modules, such as DEBS module 4, additional reductive cycle activities (a dehydratase (DH) and an enoylreductase (ER)) come into play after the module's KR performs the initial ketoreduction. The module 1 product is then passed to the module 2 KS. The module 2 AT loads the second extender unit onto the module 2 ACP, and the module 2 KS then performs the condensation to produce a triketide which is reductively processed. Additional modules come into play, each adding and processing another extender unit onto the growing polyketide chain. The final length of the polyketide chain is determined by the number of modules present in the PKS (six in the case of DEBS), and the reductive outcome at any position is determined by the complement of reductive cycle activities present in the corresponding module. After elaboration of the polyketide chain, the molecule is subjected to regiospecific cyclization by a thioesterase (TE) activity fused to the end of DEBS module 6. The macrolide product is then tailored by downstream enzymes, e.g., hydroxylases, oxidases, methyltransferases, glycosylases, and the like, to produce the final natural product.

Library Construction:

The following set of design rules applies for rationally or stochastically manipulating early biosynthetic steps in modular polyketide biosynthetic pathways. The manipulative elements include:

(1) Starter Unit.

The relaxed specificity of modular PKSs for the starter unit under in vitro conditions has been reported (Pieper et al. 1995, supra).

(2) Extender Unit.

The nature of the extender unit used by a given module is determined by the AT activity. Sequence comparisons have clearly identified the characteristics of malonyl-CoA-specific AT and methylmalonyl-CoA-specific AT activities (Haydock et al. 1995, supra) At activities using methylmalonyl-CoA or ethylmalonyl-CoA generate a chiral center having one of two possible stereochemistries. For the two common extender units, malonyl-CoA and methylmalonyl-CoA, there are thus three possible structural outcomes. (3) Reductive Cycle. The state of reduction of the O-keto group formed by KS-catalyzed condensation is governed by the set of reductive cycle activities present within the module. Thus, absence of any reductive activity yields a ketone function, while presence of only a KR activity generates an alcohol group having one of two possible stereochemistries. The presence of both KR and DH activities results in the formation of an alkene;

if a stereocenter had been generated by the AT activity, the chirality at that position is lost. The presence of the full complement of KR, DH, and ER activities results in complete reduction of the β-keto group to a methylene group. There are thus 5 theoretically possible reductive cycle outcomes at any module.

(4) Cyclizations. The linear polyketide chain may cyclize through a number of possible mechanisms. The DEBS thioesterase (TE) activity demonstrates a broad capacity to lactonize hydroxy-acids (Aggarwal et al. 1995, supra). Also, several known natural products, e.g., avermectin, mevinolin, appear to be formed through Diels-Alder cyclizations of polyketide chains containing multiple alkene groups. Cyclizations of alcohols onto ketones to form ketals and spiroketals is also commonly observed.

For any single module, therefore, there are at least 14 theoretical structural outcomes when only the two common extender units are considered. If all manipulable elements can be simultaneously controlled, there are $$S \times (14)N$$

possible polyketide chains which can be produced from an N-module PKS using S starter units. For a 6-module PKS such as DEBS, $14^6$, or more than $7.5 \times 10^6$ polyketide chains could be produced using a single starter unit. Furthermore, enzymes that catalyze downstream modifications, e.g., cyclizations, group-transfer reactions, oxidoreductions, and the like, can be studied along the lines presented herein and elsewhere. It is therefore possible that at least some of these degrees of freedom can be combinatorially exploited to generate libraries of synthetic products with structural diversity that is comparable to that observed in nature.

Although modular PKSs have not been extensively analyzed, the one-to-one correspondence between active sites and product structure, together with the incredible chemical diversity observed among naturally occurring "complex" polyketides, indicates that the combinatorial potential within these multienzyme systems could be considerably greater than that for aromatic PKSs. For example, a wider range of primer units including aliphatic monomers (acetate, propionate, butyrate, isovalerate, etc.), aromatics (aminohydroxybenzoic acid), alicyclics (cyclohexanoic acid), and heterocyclics (pipecolic acid) are found in various macrocyclic polyketides. Recent studies have shown that modular PKSs have relaxed specificity for their starter units (Kao et al. *Science* (1994), supra). The degree of β-ketoreduction following a condensation reaction can also be altered by genetic manipulation (Donadio et al. *Science* (1991), supra; Donadio, S. et al. *Proc. Natl. Acad. Sci. USA* (1993) 90:7119–7123). Likewise, the size of the polyketide product can be varied by designing mutants with the appropriate number of modules (Kao, C. M. et al. *L. Am. Chem. Soc.* (1994) 116:11612–11613). Modular PKSs also exhibit considerable variety with regards to the choice of extender units in each condensation cycle, although it remains to be seen to what extent this property can be manipulated. Lastly, these enzymes are particularly well-known for generating an extensive range of asymmetric centers in their products in a highly controlled manner. Thus, the combinatorial potential within modular PKS pathways could be virtually unlimited.

c) Glycosylation

Both aromatic and complex polyketides are often glycosylated. In many cases (e.g., doxorubicin and erythromycin) absence of the sugar group(s) results in considerably weaker bioactivity. There is tremendous diversity in both the types and numbers of sugar units attached to naturally occurring polyketide aglycones. In particular, deoxy- and aminosugars are commonly found. Regiochemical preferences can be detected in many glycosylated natural products. Among anthracyclines, O-17 is frequently glycosylated, whereas among angucyclines, C-10 is usually glycosylated. Glycosyltransferases involved in erythromycin biosynthesis may have relaxed specificities for the aglycone moiety (Donadio, S. et al. *Science* (1991) 252:675–679). An elloramycin glycosyltransferase may be able to recognize an unnatural NDP-sugar unit and attach it regiospecifically to an aromatic polyketide aglycone (Decker, H. et al. *Angew. Chem.* (1995), in press). These early results suggest that glycosyltransferases derived from secondary metabolic pathways have unique properties and may be attractive targets for use in the generation of combinatorial libraries.

d) Fungal PKS

Like the actinomycetes, filamentous fungi are a rich source of polyketide natural products. The fact that fungal PKSs, such as the 6-methylsalicylic acid synthase (6-MSAS) and the mevinolin synthase, are encoded by single multi-domain proteins (Beck et al. *Eur. J. Biochem.* (1990), supra; Davis, R. et al. *Abstr. Genet. Ind. Microorg. Meeting*, supra) indicates that they may also be targeted for combinatorial mutagenesis. Moreover, fungal PKSs can be functionally expressed in S. coelicolor CH999 using the genetic strategy outlined above and described in WO 95/08548, supra. Chain lengths not observed in bacterial aromatic polyketides (e.g., tetraketides, pentaketides and hexaketides) have been found among fungal aromatic polyketides (O'Hagan, D. The Polyketide Metabolites (Ellis Horwood, Chichester, U. K., 1991). Likewise, the cyclization patterns of fungal aromatic polyketides are quite different from those observed in bacterial aromatic polyketides (Id.). In contrast with modular PKSs from bacteria, branched methyl groups are introduced into fungal polyketide backbones by S-adenosylmethionine-dependent methyltransferases; in the case of the mevinolin PKS (Davis, R. et al. *Abstr. Genet. Ind. Microorg. Meeting*, supra), this activity is encoded as one domain within a monocistronic PKS. It is now possible to experimentally evaluate whether these and other sources of chemical diversity in fungal polyketides are indeed amenable to combinatorial manipulation.

e) Summary:

The number of potentially novel polyketides that can be catalytically produced by PKS gene products in a cell-free system increases geometrically as new degrees of freedom are exploited and/or protein engineering strategies are brought to bear on the task of creating enzyme subunits with specificities not observed in nature. For example, non-acetate starter units can be incorporated into polyketide backbones (e.g., propionate in daunorubicin and malonamide in oxytetracycline). Furthermore, enzymes that catalyze downstream cyclizations and late-step modifications, such as group transfer reactions and oxidoreductions commonly seen in naturally occurring polyketides, can be studied along the lines presented here and elsewhere. It is therefore possible that at least some of these degrees of freedom can be combinatorially exploited to generate libraries of synthetic products with structural diversity that is comparable to that observed in nature.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

The Examples provided below describe recombinant production of a modular PKS and methods for in vitro synthesis of polyketides by recombinant DEBS and by an active deletion mutant. The latter mutant, designated "DEBS 1+2+ TE", contains the first two modules from DEBS 1 fused to the thioesterase domain normally found at the C-terminal end of module 6 of DEBS (FIG. 1). Both DEBS and DEBS 1+2+TE have been successfully expressed in *S. coelicolor* CH999, purified, and used in a cell-free system for the in vitro catalytic synthesis of, respectively, 6-dEB (1).

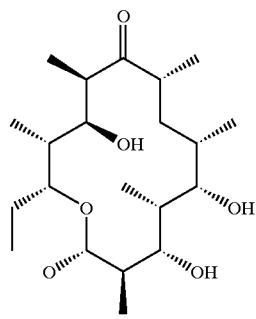

(1)

and (2R,3S,4S,5R)-2,4-dimethyl-3,5-dihydroxy-n-heptanoic acid 6-lactone (2).

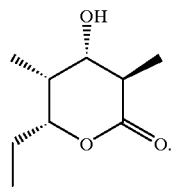

(2)

Three open reading frames (eryAI, eryAII, and eryAIII) encode the DEBS polypeptides and span 32 kb in the ery gene cluster of the *Saccharopolyspora erythraea* genome. The genes are organized in six repeated units, each designated a "module" (see FIG. 1). Each module encodes a set of active sites that, during polyketide biosynthesis, catalyzes the condensation of an additional monomer onto the growing chain. Each module includes an acyltransferase (AT), β-ketoacyl carrier protein synthase (KS), and acyl carrier protein (ACP) as well as a subset of reductive active sites (β-ketoreductase (KR), dehydratase (DH), enoyl reductase (ER)). The number of reductive sites within a module corresponds to the extent of β-keto reduction in each condensation cycle. The thioesterase (TE) encoded at the end of module appears to catalyze lactone formation.

Due to the large sizes of eryAI, eryAII, and eryAIII, and the presence of multiple active sites, these genes can be conveniently cloned into a plasmid suitable for expression in a host cell, such as the genetically engineered host cell CH999, using an in vivo recombination technique. This technique, described in WO 95/08548 utilizes derivatives of the plasmid pMAK705 (Hamilton et al. (1989) *J. Bacteriol.* 171:4617) to permit in vivo recombination between a temperature-sensitive donor plasmid, which is capable of replication at a first, permissive temperature and incapable of replication at a second, non-permissive temperature, and recipient plasmid. The eryA genes thus cloned gave pCK7, a derivative of pRM5 (McDaniel et al. (1993) *Science* 262:1546). A control plasmid, pCK7f, was constructed to carry a frameshift mutation in eryAI. pCK7 and pCK7f possess a ColEI replicon for genetic manipulation in *E. coli* as well as a truncated SCP2* (low copy number) Streptomyces replicon. These plasmids also contain the divergent actI/actIII promoter pair and actII-ORF4, an activator gene, which is required for transcription from these promoters and activates expression during the transition from growth to stationary phase in the vegetative mycelium. High-level expression of PKS genes occurs at the onset of stationary phase of mycelial growth.

EXAMPLE 1

Production of *S. coelicolor* CH999

An *S. coelicolor* host cell, genetically engineered to remove the native act gene cluster, and termed CH999, was constructed using *S. coelicolor* CH1 (Khosla et al. *Molec. Microbiol.* (1992), supra) as described in WO95/08548, incorporated herein by reference. *S. coelicolor* CH999 lacks the entire ACT gene cluster.

EXAMPLE 2

Production of the Recombinant Vector DRM5

Shuttle plasmids are used to express recombinant PKSs in CH999. Such plasmids typically include a colEI replicon, an appropriately truncated SCP2* Streptomyces replicon, two act-promoters to allow for bidirectional cloning, the gene encoding the actII-ORF4 activator which induces transcription from act promoters during the transition from growth phase to stationary phase, and appropriate marker genes. Restriction sites have been engineered into these vectors to facilitate the combinatorial construction of PKS gene clusters starting from cassettes encoding individual subunits (or domains) of naturally occurring PKSs. Among the many advantages of this method are that (i) all relevant biosynthetic genes are plasmid-borne and therefore amenable to facile manipulation and mutagenesis in *E. coli* and (ii) the entire library of PKS gene clusters can be expressed in the same bacterial host.

pRM5 was the shuttle plasmid used for expressing PKSs in CH999. It includes a ColEI replicon to allow genetic engineering in *E. coli*, an appropriately truncated SCP2* (low copy number) Streptomyces replicon, and the actII-ORF4 activator gene from the act cluster, which induces transcription from act promoters during the transition from growth phase to stationary phase in the vegetative mycelium. pRM5 carries the divergent actI/actIII promoter pair, together with convenient cloning sites to facilitate the insertion of a variety of engineered PKS genes downstream of both promoters. pRM5 lacks the par locus of SCP2*; as a result the plasmid is slightly unstable (approx. 2% loss in the absence of thiostrepton). This feature was deliberately introduced in order to allow for rapid confirmation that a phenotype of interest could be unambiguously assigned to the plasmid-borne mutant PKS. The recombinant PKSs from pRM5 are expressed approximately at the transition from exponential to stationary phase of growth, in good yields. pRM5 was constructed as described in WO95/08548.

EXAMPLE 3

Construction of Expression Vectors for, and Expression of Aromatic PKS

WO95/08548 describes the construction of expression vectors using the pRM5 host plasmid using portions of the aromatic polyketide synthase gene clusters of actinorhodin (act), granaticin (gra) and tetracenomycin (tcm) gene clusters. A number of hybrid clusters are described. These hybrid clusters were introduced into S. coelicolor CH999 and expressed to produce the relevant polyketide synthases which in turn produce a variety of polyketides. Additional constructs using genes derived from the frenolicin B (fren) PKS gene cluster were also prepared.

EXAMPLE 4

Production of Modular PKS

Expression plasmids containing recombinant modular DEBS PKS genes were constructed by transferring DNA incrementally from a temperature-sensitive "donor" plasmid, i.e., a plasmid capable of replication at a first, permissive temperature and incapable of replication at a second, non-permissive temperature, to a "recipient" shuttle vector via a double recombination event, as described in WO95/08548, and in Kai et al. Science (1994) 265:509. pCK7, contains the complete eryA gene. A control plasmid, pCK7f, which contains a frameshift error in eryAI, was constructed in a similar manner. pCK7 and pCK7f were transformed into E. coli ET12567 (MacNeil (1988) J. Bacteriol. 170:5607) to generate unmethylated plasmid DNA and subsequently moved into S. coelicolor CH999 using standard protocols (Hopwood et al. (1985) Genetic manipulation of Streptomyces. A laboratory manual. The John Innes Foundation: Norwich).

Upon growth of CH999/pCK7 on R2YE medium, two polyketides were produced. In addition, three high-molecular-weight proteins (>200 kDa) presumably DEBS1, DEBS2 and DEBS3 (Caffrey et al. FEBS Lett. (1992) 304:225) were also observed in crude extracts of CH999/pCK7 via sodium dodecyl sulfate-polyacrylamide gel electrophoresis ("SDS-PAGE"). No polyketide products were observed from CH999/pCK7F.

EXAMPLE 5

Recombinant Production of a Mutant DEBS PKS

In this Example a deletion mutant PKS was constructed that consists of DEBS1 fused to the TE of DEBS3 ("DEBS 1+2+TE"); plasmid pCK12 contained the genes encoding the DEBS 1+2+TE.

The DEBS 1+2+TE PKS contained a fusion of the carboxy-terminal end of the acyl carrier protein of module 2 (ACP-2) to the carboxy-terminal end of the acyl carrier protein of module 6 (ACP-6) (see FIG. 1). Thus ACP-2 is essentially intact in this PKS and is followed by the amino acid sequence naturally found between ACP-6 and the TE. pCK12 is identical to pCK7 (Kao et al. Science (1994), supra) with the exception of a deletion between the carboxy-terminal ends of ACP-2 and ACP-6. The fusion occurs between residues L3455 of DEBS1 and Q2891 of DEBS3. An SpeI site is present between these two residues so that the DNA sequence at the fusion is CTCACTAGTCAG.

EXAMPLE 6

Preparation of Cell-Free DEBS from pCK7 and pCK12

The DEBS preparation was carried out as follows. S. coelicolor CH999/pCK12 or CH999/pCK7 cells were harvested after a growth of 55 h in liquid cultures. Typically, 8–10 grams of cells (wet cell weight) were disrupted using sonication (5×30 s bursts). The resultant cell slurry was ultracentrifuged (2 h at 192,000×g) and nucleic acids precipitated with 0.2% polyethyleneimine (Step 1) yielding about 200 mg total protein. All 3 DEBS proteins were precipitated in a 55% saturated ammonium sulfate solution. The incubation buffer (buffer I) used thereafter contained 150 mM sodium phosphate buffer (pH 7.1), 15% glycerol, 2 mM dithiothreitol ("DTT"), and 2 mM ethylene diamine tetraacetic acid ("EDTA"). After desalting on Sephadex G25 M (Step 2), about 30 mg protein (15–20 mg/mL) was applied to an Agarose BioGel A size exclusion column (140 mL). Fractions containing DEBS proteins were pooled and concentrated to 1 mg/mL on YM 30 ultrafiltration membranes (Step 3).

Figure 3A:
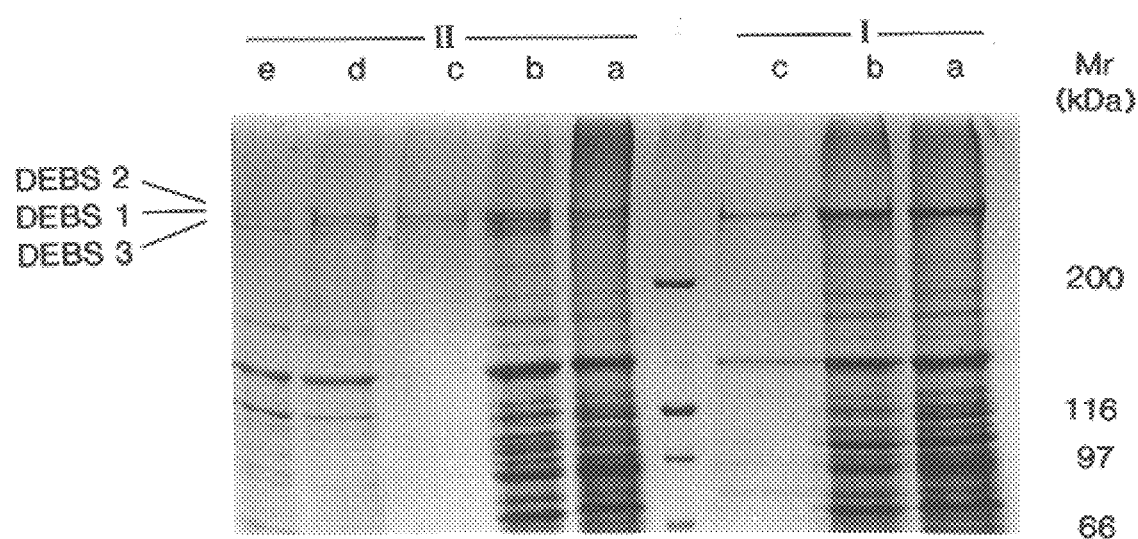
FIG. 3A depicts a Coomassie Blue-stained 5% acrylamide gel of protein fractions containing DEBS 1+2+thioesterase (DEBS 1+2+TE) from pCK12 or the complex of DEBS 1, 2, and 3 from pCK7. Lanes Ia, Ib and Ic show DEBS 1+2+TE after purification Step 1 (a), after Step 2 (b) and after Step 3 (c). Lanes IIa, IIb, IIc, IId and IIe show DEBS 1, 2, and 3 after Step 1 (a), after Step 2 (b), after Step 3 (c), (d) and (e) in order of increasing elution volume.

DEBS proteins were detected by their high molecular weights of 330 kDa (DEBS 3), 370 kDa (DEBS 1) and 380 kDa (DEBS 2) by SDS-PAGE; these proteins were absent in cell extracts of a variety of control strains. The apparent molecular weights of the DEBS proteins were also evaluated by gel filtration on a Superose 6 HR 10/30 column (Pharmacia), using thyroglobulin (669 kDa) and apoferritin (443 kDa) as high molecular weight markers. (see FIG. 3A).

Recombinant DEBS proteins isolated from cell extracts were partially purified as described above. Size exclusion chromatography of a crude extract containing the three DEBS subunits on Biogel A and Superose 6 (upper size exclusion limit 15 MDa and 1.5 MDa, respectively) revealed that DEBS 1 and 2 associate more tightly with each other than with DEBS 3. Moreover, DEBS 1 and 2 (370 kDa and 380 kDa, respectively) elute over a wide range of fractions corresponding to $M_r$ between 10 and 1 MDa, indicating that they might form a multimeric complex, which partially dissociates during gel filtration. DEBS 3, however, is not present in this extremely large $M_r$ range. From size calibration experiments on a Superose 6 column, DEBS 3 (330 kDa) mostly elutes as a dimer (similar to thyroglobulin, 669 kDa). Upon concentration, the Biogel A column fractions (see FIG. 3A) containing DEBS 1 and 2 alone were found be inactive in vitro. However, when pooled with a concentrated fraction containing DEBS 3 alone (FIG. 3A), the reconstituted complex of the three proteins showed comparable activity to the DEBS 1, 2, and 3 preparation derived via ammonium sulfate precipitation of the crude cell extract. These purification results suggest that activity of DEBS requires the formation of a high molecular weight oligomeric complex, possibly a trimer of dimers. The formation of homodimers by purified (but not fully active) DEBS subunits has been reported (Aparicio et al. J. Biol. Chem.

(1994), supra; Bevitt et al. *Eur. J. Biochem.* (1992), supra; Caffrey et al. *Eur. J. Biochem.* (1991), supra; and Leadlay et al. *Biochem. Soc. Trans.* (1993), supra).

Figure 3B:
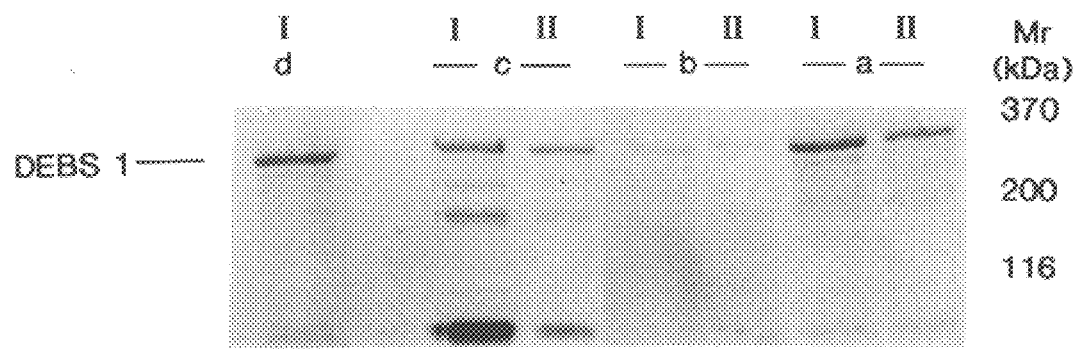
FIG. 3B depicts an autoradiogram showing the covalent modification of DEBS 1, 2, and 3 (Lanes I a–d) or DEBS 1+2+TE (Lanes II a–c) by $^{14}$C-labeled starter units $[1-^{14}C]$ propionyl-CoA (20 μM) (Lanes Ia and IIa), $[1-^{14}C]$butyryl-CoA (160 μM) (Lanes Ib and IIb), $[1-^{14}C]$acetyl-CoA (40 μM) (Lanes Ic and IIc) and $[1-^{14}C]$propionyl-CoA (20 μM) after a 30 min-preincubation with iodoacetamide (1 Mm) (Lane Id).

The covalent modification of the cell-free DEBS preparations by $^{14}$C-labeled starter units in the absence of chain extension reactions is depicted in FIG. 3B. Partially purified DEBS preparations (40 mg total protein) were incubated with the substrates [1-$^{14}$C]propionyl-CoA (20 μM), [1-$^{14}$C] butyryl-CoA (160 μM), [1-$^{14}$C]acetyl-CoA (40 μM), or [1-$^{14}$C]propionyl-CoA (20 μM) including a 30-min preincubation with iodoacetamide (1 mM). After, denaturation and separation of the proteins in a SDS-PAGE (5%), the separated proteins were electrotransferred onto a nitrocellulose membrane, $^{14}$C-labeled proteins were exposed to an X-ray film for 5 days.

EXAMPLE 7

Cell-Free Synthesis of 6-dEB and (2R,3S,4S,5R)-2,4-dimethyl-3,5-dihydroxy-n-heptanoic acid δ-lactone In order to establish an in vitro assay system for polyketide synthesis, partially purified preparations of the complete DEBS 1, 2, and 3 system and of DEBS 1+2+TE, prepared as described in Example 6, were incubated with their natural substrates [1-$^{14}$C]propionyl-CoA, (2RS)-methylmalonyl-CoA, and NADPH.

The DEBS 1+2+TE and DEBS 1, 2, and 3 preparations described in the Example 6 (purification Step 2) were adjusted to a concentration of 8 mg total protein/mL buffer. Incubations were carried out at 28° C. with the [1-$^{14}$C] propionyl-CoA (specific activity 50 Ci/mol, 10 μM), methylmalonyl-CoA (250 μM), and NADPH (500 μM) dissolved in buffer I in a volume of 250 μL for 3 h. Thereafter, the incubation mix was extracted with 2×2 mL ethyl acetate, the ethyl acetate was evaporated of, and the product was analyzed by thin layer chromatography ("TLC") in 60% ethyl acetate/40% hexane followed. The TLC plate was exposed to an X-ray film for 2 days.

Lanes Ia and Ib of the autoradiogram (FIG. 4) show extracts of DEBS 1+2+TE including [1-$^{14}$C]propionyl-CoA and NADPH but excluding methylmalonyl-CoA (Ia) and including all 3 substrates (Ib). Lanes IIa, IIb and IIc of the autoradiogram (FIG. 4) show incubations of DEBS 1, 2, and 3 including [1-$^{14}$C]propionyl-CoA and NADPH but excluding methylmalonyl-CoA (IIa), including all 3 substrates (IIb) and preincubation of DEBS 1, 2, and 3 with cerulenin (100 μM) for 15 min, followed by addition of all 3 substrates (IIc). Ethyl acetate/hexane (50:50) was used as the solvent system. In lane Ib the major labeled component is identical in $R_f$ (0.30) to authentic triketide (2) (see arrow), while in lane IIb, the least polar labeled product is identical in $R_f$ (0.40) to authentic 6-dEB (1) (see arrow). In lanes Ib and IIb the concentrations of the minor products (but not 6-dEB nor the triketide lactone) vary substantially as a function of the DTT concentration in the reaction buffer; the structures of these DTT-dependent products are under investigation. Control experiments were also performed with DEBS 1+2+TE, with complete DEBS in the absence of NADPH, and with comparable cell-free preparations from CH999 and from CH999/pSEK38 (a recombinant strain that expresses the actinorhodin PKS gene cluster). In all four controls, neither 6-dEB nor the triketide lactone were detected. The intense, more polar band, evident lanes IIa, IIb and IIc was also present in all the above null controls including extracts obtained from CH999 alone. The identities of the enzymatically generated [$^{14}$C)-(I) and [$^{14}$C]-(2) were each confirmed by dilution of the respective TLC-purified product with authentic unlabeled carrier and recrystallization to constant activity. Thus labeled 6-dEB, from incubation of [1-$^{14}$C] propionyl-CoA with DEBS 1, 2, and 3, mixed with 15.4 mg of (1), was recrystallized 4 times from ether/hexane. After each recrystallization, two to three portions of each sample were analyzed by liquid scintillation counting: 2132±16 dpm/mg (1st recryst); 2117±23 dpm/mg (2nd recryst); 2125±2 dpm/mg (3rd recryst); 2141±17 dpm/mg (4th recryst); (mean $^{14}$C act. 2129±9 dpm/mg). Similarly labeled triketide, from incubation of [1-$^{14}$C]propionyl-CoA with DEBS 1+2+TE, was mixed with 20.4 mg of unlabeled (2) and recrystallized 4 times from ether/hexane: 4528±306 dpm/mg (1st recryst); 4725±80 dpm/mg (2nd recryst); 4662±74 dpm/mg (3rd recryst); 4706±60 dpm/mg (4th recryst); (mean $^{14}$C act. 4655±77 dpm/mg).

Figure 4:
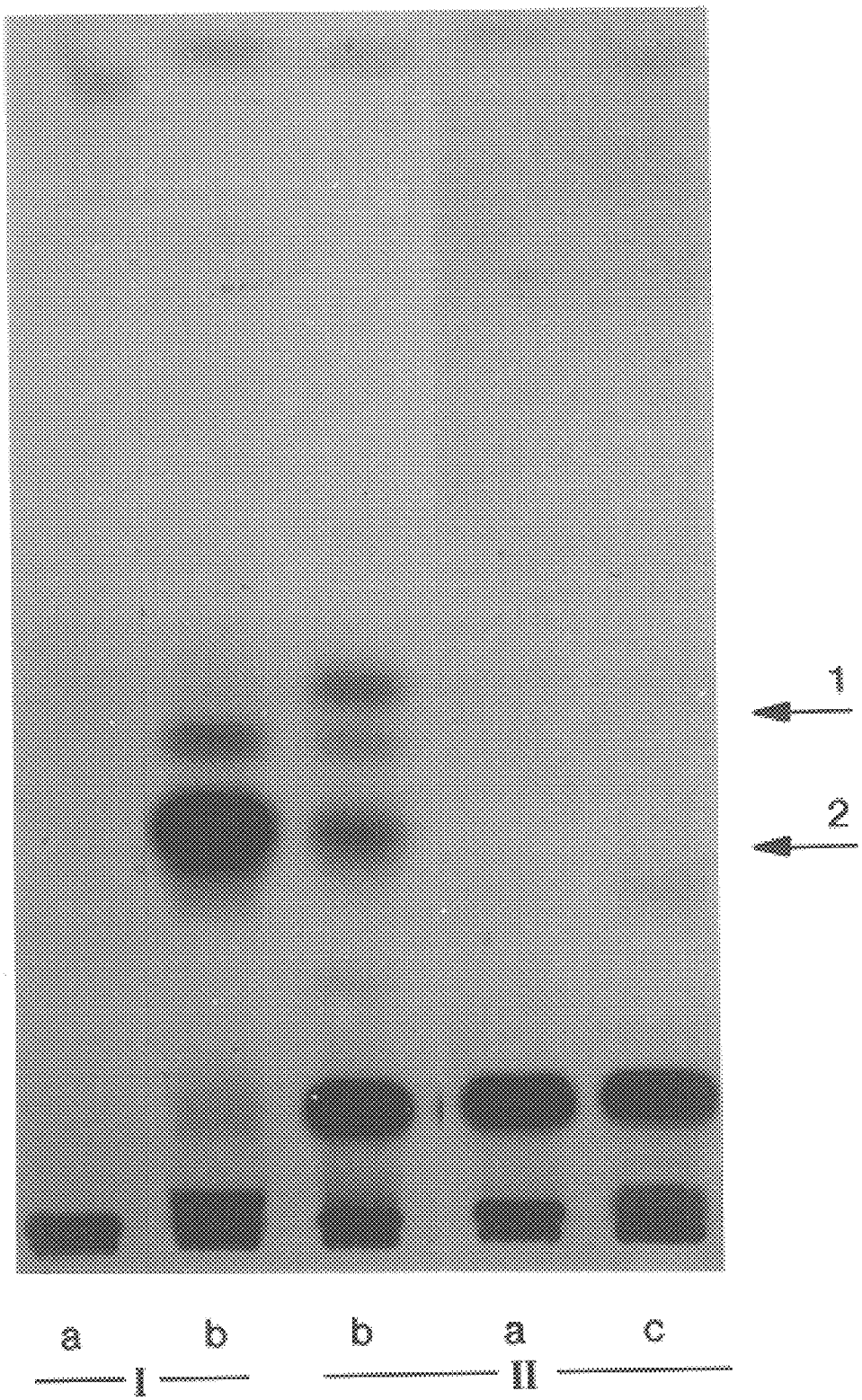
FIG. 4 depicts an autoradiogram showing in vitro synthesis of $^{14}$C-labeled 6-DEB (1) and the triketide lactone (2).
Figure 5:
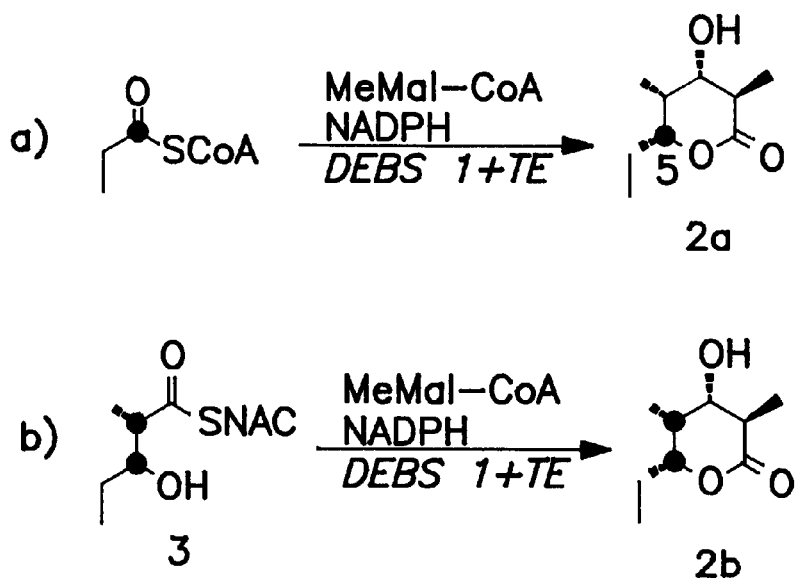
FIG. 5 is a pictorial representation of the conversion of $[1-^{13}C]$ propionyl-CoA to triketide lactone (2a) by DEBS 1+2+TE (a) and the conversion of $[2,3-^{13}C_2]$-(2S,3R)-2-methyl-3-hydroxypentanoyl-NAC thioester (3) triketide lactone (2b) by DEBS 1+2+TE (b).

These results indicate that each cell-free DEBS protein preparation synthesized a $^{14}$C-labeled product with TLC $R^f$ values identical to those of reference samples of either 6-dEB (1) or (2R,3S,4S,5R)-2,4-dimethyl-3,5-dihydroxy-n-heptanoic acid 6-lactone (2), respectively, as evidenced by TLC-autoradiography (FIG. 4). The identities of ($^{14}$C)-(1) and [$^{14}$C]-(2) were confirmed by dilution of each of the TLC-purified radiolabeled products with authentic unlabeled carrier 6-dEB or triketide lactone and repeated recrystallization of each sample to constant activity. The formation of each lactone product showed an absolute requirement for the relevant protein preparation as well as for methylmalonyl-CoA and NADPH and was inhibited by both N-ethylmaleimide and cerulenin, both well-known inhibitors of the condensation reactions of fatty acid biosynthesis (Plate, C. A. et al. *J. Biol. Chem.* (1970) 245:2868; D'Agnolo, G. et al. *Biochim. Biophys. Acta* (1973) 326:155; Kauppinen, S. et al. *Carlsberg Res. Commun.* (1988) 53:357–370). Based on the observed radiochemical yield of purified product, the formation of 6-dEB catalyzed by DEBS 1, 2, and 3 was estimated to be 33 pmol/mg total protein. By comparison, the formation of (2) by DEBS 1±2+TE was 600 pmol/mg total protein.

The specificity of labeling in the triketide lactone product was unambiguously confirmed by preparative scale incubation of [1-$^{13}$C]propionyl-CoA with DEBS 1+2+TE in the presence of methylmalonyl-CoA and NADPH. Analysis of the derived product (2a) (see FIG. 4 (a)) by 100 MHz $^{13}$C NMR showed an enhanced peak at 81.3 ppm corresponding to enrichment at the predicted site, C-5, in (2R,3S,4S,5R)-2,4-dimethyl-3,5-dihydroxy- n-heptanoic acid 8-lactone (Kao, C. M. et al. *J. Am. Chem. Soc.* (1994), supra).

EXAMPLE 8

Substrate Specificity of DEBS 1+2+TE In a Cell-Free System

The in vitro assays were carried out as described in Example 6, substituting [1-$^{14}$C]propionyl-CoA by either (1-$^{14}$C]butyryl-CoA (160 μM) or [1-$^{14}$C)acetyl-CoA, 40 μM. Incubations of DEBS 1+2+TE (purification Step 2) were performed excluding methylmalonyl-COA or including methylmalonyl-CoA and NADPH in addition to the appropriate $^{14}$C-labeled primer substrate. Alternatively, DEBS 1+2+TE was preincubated with 1 mM N-ethylmaleimide before addition of all 3 substrates. Control experiments carried out in the absence of NADPH as well as with an equivalent protein preparation from *S. coelicolor* CH999 did not yield the observed labeled products. Ethyl acetate/hexane (60:40) was used as the solvent system.

Figure 6B:
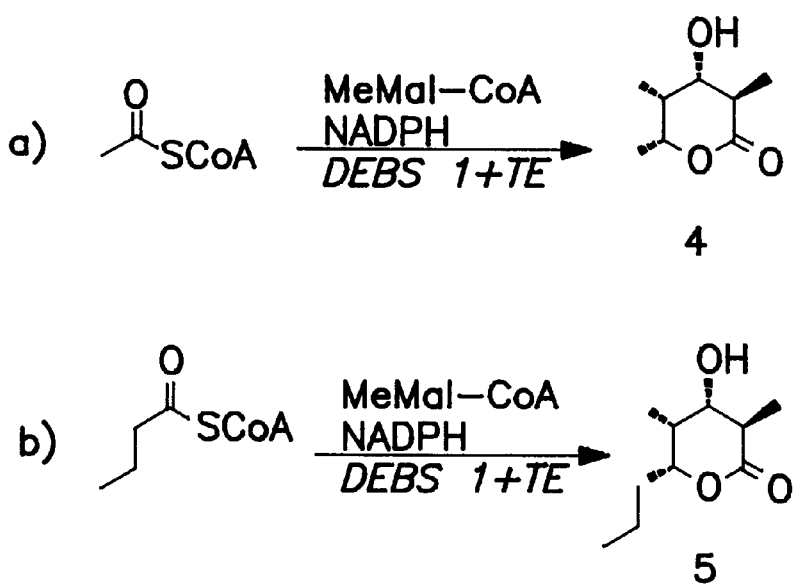
FIG. 6B is a pictorial representation of the conversion of acetyl-CoA to compound (4) by DEBS 1+2+TE (a) and the proposed conversion of butyryl-CoA to compound (5) by DEBS 1+2+TE (b).
Figure 6A:
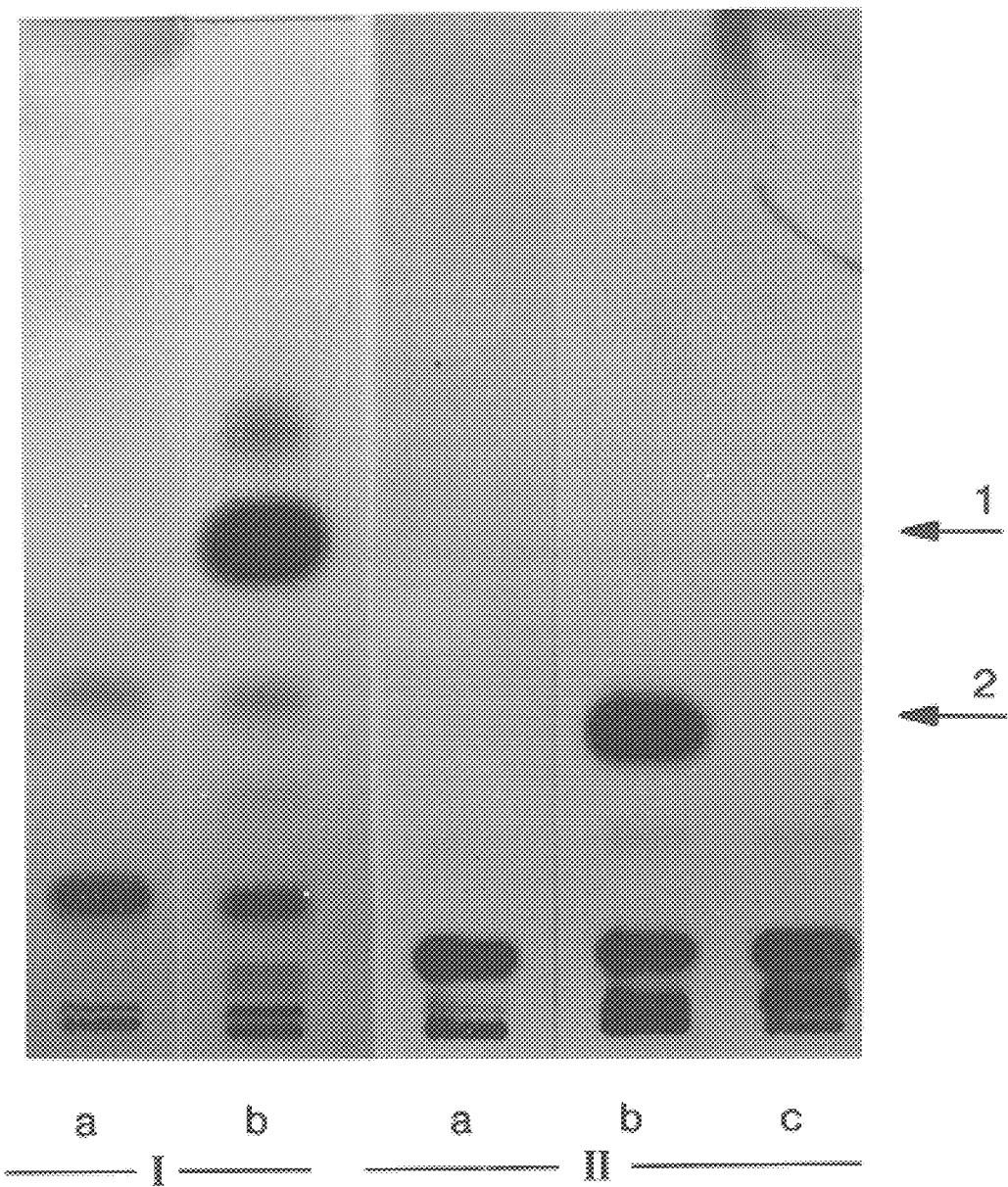
FIG. 6A depicts a thin layer chromatography-autoradiogram showing the incorporation of alternative substrates into polyketide products. Lane Ib contains the putative $C_{10}$-lactone homolog (5) (see FIG. 5B), $R_f$=0.36 (marked by arrow 1). Lane IIb contains (4) (see FIG. 5B), $R_f$=0.23, (marked by arrow 2, identical to the $R_f$ of an authentic sample of compound (4).

Development of the above radiochromatographic assay has allowed a preliminary analysis of the substrate specificity of these multifunctional enzyme complexes. For example, DEBS 1+2+TE appears to exhibit a relaxed specificity for primer unit analogs, as shown by both protein acylation and product formation. In addition to the expected acylation by [1-$^{14}$C]propionyl-CoA, both DEBS 1+2+TE and DEBS 1 (from the mixture of DEBS 1, 2, and 3) also form covalent adducts with [1-$^{14}$C]acetyl-CoA and [1-$^{14}$C]butyryl-CoA (see FIG. 3B). Since the protein labeling is unaffected by the presence of active site thiol inhibitors such as iodoacetamide, the substrates are presumably bound to the "loading" acyltransferase domain at the N-terminal end of DEBS 1. All three acyl-CoA substrates appear to react with DEBS 1 or DEBS 1+2+TE with comparable efficiencies. (The apparently lower intensity of the butyryl-CoA-labeled band in FIG. 3B is due to the 10-fold lower specific activity of (1-$^{14}$C]butyryl-CoA.) In the presence of methylmalonyl-CoA and NADPH, both acetyl-CoA and butyryl-CoA serve as surrogate polyketide chain initiators for DEBS 1+2+TE, giving rise to compound (4) (see FIG. 6B) the previously described $C_8$ analog of compound (2), and what is presumed to be compound (5) (see FIG. 6B), the $C_{10}$ homolog of (2), respectively, as judged by thin layer chromatography-autoradiography (see FIG. 6A).

In addition to the above CoA thioesters, DEBS 1+2+TE enzyme can also process the N-acetylcysteamine thioester of the polyketide chain elongation intermediate, (2S,3R)-2-methyl-3-hydroxypentanoyl-NAC thioester (3). Thus incubation of (1-$^{14}$C]-(3) (Cane, D. E. et al. *J. Am. Chem. Soc.* (1981) 103:5960; Cane, D. E. et al. *Tetrahedron* (1983) 39:3449; Cane, D. E. et al. *J. Am. Chem. Soc.* (1986) 108:4957; Cane, D. E. et al. *J. Am. Chem. Soc.* (1987) 109:1255; Cane, D. E. et al, *Tetrahedron Lett.* (1991) 32:5457; and Cane, D. E. et al. *J. Antibiot.* (1995) 48:647–651 (1995)) with DEBS 1+2+TE in the presence of methylmalonyl-CoA and NADPH gave rise to a labeled product which had the chromatographic mobility expected for the triketide lactone (2) and which could be recrystallized to constant activity when diluted with unlabeled triketide lactone, as described above. The specificity of labeling was unambiguously confirmed by preparative scale incubation of [2,3-$^{13}C_2$]-(3) with DEBS 1+2+TE, methylmalonyl-CoA and NADPH. The $^{13}$C NMR spectrum of the resulting triketide lactone (2b) (see FIG. 4) displayed a pair of enhanced and coupled doublets ($J_{CC}$=34.5 Hz) centered at 36.7 and 81.3 ppm, corresponding to enrichment at each of the expected sites of labeling, C-4 and C-5, respectively. This result is consistent with the previously reported incorporation of [2,3-l3$c_2$]-(3) into the erythromycin macrolide (Cane et al. *J. Am. Chem. Soc.* (1981), supra; Cane et al. Tetrahedron (1983), supra; Cane et al. *J. Am. Chem. Soc.* (1986), supra; Cane et al. *J. Am. Chem. Soc.* (1987), supra; Cane et al. *Tetrahedron Lett.* (1991), supra) in intact cell experiments, as well as the results of numerous experiments in which NAC thioesters of advanced intermediates of polyketide chain elongation have been shown to be incorporated into other polyketides.

The Examples provided herein lend further credence to the speculation that these NAC thioesters are directly loaded on to the appropriate active site in the PKS, and do not require the participation of additional proteins or cofactors. This experiment also confirms directly the ability of the macrolide synthase to recognize exogenously added chain elongation intermediates and load them correctly on the cognate PKS module for further processing to the natural product.

EXAMPLE 9

Cell-Free Synthesis of 2,4-Dimethyl-5-ethyl-3-hydroxy-2-pyrone

The DEBS1+2+TE preparation described in Example 6 (purification step 2) was used as described in Example 7 but without the addition of NADPH to the reaction mixture. This reaction produced 2,4-dimethyl-5-ethyl-3-hydroxy-2-pyrone as demonstrated by NMR analysis.

The following Examples provide methods for inhibiting the synthesis of polyketides in a modular PKS from natural first-module starter units or from such starter units derived from the decarboxylation of extender units in so far as such substrates compete with unnatural starter units. The method involves inhibiting the loading of the first module of a PKS with a natural starter unit by inactivating a key active site on which starter units are loaded, for example, by deleting the KS1 or otherwise rendering KS1 nonfunctional or, alternatively, by deleting or rendering nonfunctional the ACP1. In a cell-free system, wherein the synthesis of a polyketide from unnatural starter units is desired, this method provides the advantage of minimizing undesirable competitive polyketide synthesis based on the presence of the natural starter and/or extender units. In addition, the method spares the extender units which would otherwise be supplied in a cell-free system at a considerable cost. This method is also of particular importance in an in vivo system in which the production of desired polyketides from unnatural substrates may be inhibited by the presence of natural substrates, thereby precluding the efficient use of the unnatural starter units to yield the desired product.

EXAMPLE 10

Construction, Expression and Analysis of [KS1*]-DEBS1+2+TE

In the absence of added propionyl-CoA, DEBS1+2+TE can form the propionyl starter unit through decarboxylation of methylmalonyl-loaded enzyme. This reaction requires a functional module 1 KS activity, which decarboxylates loaded methylmalonate in order to condense the extender unit with the starter unit. In the absence of supplied propionyl-CoA starter unit, the decarboxylated extender unit can be transferred backwards, allowing the loading of a second methylmalonyl-CoA extender and subsequent formation of a diketide. As this back-formation of propionyl units is undesirable when alternative starter units are being supplied to the system, a mutant of DEBS1+2+TE in which the module 1 KS has been inactivated through site-directed mutagenesis was prepared. The KS1 sequence was altered such that the active site cysteine residue (in the signature sequence cys-ser-ser-ser-leu) was replaced by alanine. The resulting expression plasmid, designated pKAO179, encodes a 2-module PKS which is inactive under the standard reaction conditions (propionyl-CoA, methylmalonyl-CoA, and NADPH). Inactivation of KS1 thus prevents the back formation of propionyl units, but also prevents diketide formation. When this protein is supplied with diketide thioester, i.e., (2S,3R)-2-methyl-3-hydroxy-pentanoyl N-acetylcysteamine thioester, methylmalonyl-CoA, and NADPH, however, the triketide product (2R,3S,4S,5R)-2,4-dimethyl-3,5-dihydroxyheptanoic δ-lactone is produced. This construct allows the in vitro production of triketides having unusual starter units through use of the corresponding diketide thioesters, uncontaminated by the normal triketide product.

EXAMPLE 11

In Vivo Production of Novel Polyketides by Fermentation Using [KS1*]DEBS Mutants As described in Example 10, the module β-ketoacylsynthase (KS1) activity of DEBS can be inactivated through site-directed mutagenesis. This mutation can be introduced into any combination of modules to produce a set of DEBS-backed PKSs which are incompetent for polyketide synthesis unless supplied with a suitable diketide thioester, e.g., 2-methyl-3-hydroxypentanoyl N-acetylcysteamine thioester or analogs. The method described in Example 10 can be extended to allow for the in vivo production of novel polyketides through feeding of the appropriate diketide thioester analogs to actively growing cultures of S. coelicolor CH999 containing [KS1*]-DEBS-based expression plasmids. The corresponding diketide as a free carboxylic acid may also be fed to the cultures if the cellular thioesterification system is functional on the acid, and if the cells are permeable to the acid. For example, the in vivo production of (2R,3S,4S,5R)-2,4-dimethyl-3,5-dihydroxy-n-heptanoic acid 6-lactone is described above.

A culture of S. coelicolor CH999/pKAO179 is established by inoculation of 200 mL of SMM medium (5% PEG-800, 0.06% $MgSO_4$, 0.2% $(NH_4)_2SO_4$, 25 mM TES, pH 7.2, 25 mM $KH_2PO_4$, 25 mM $K_2HPO_4$, 1.6% glucose, 0.5% casamino acids, trace elements) with spores. The culture is incubated at 30° C. with shaking at 325 rpm. A solution of (2S,3R)-2-methyl-3-hydroxypentanoyl N-acetylcysteamine thioester (100 mg) and 4-pentynoic (15 mg) in 1 mL of methylsulfoxide is added to the culture in three parts: after 50 hours (400 mL); after 62 hours (300 mL); and after 86 hours (300 mL). After a total of 144 hours, the culture is centrifuged to remove mycelia. The fermentation broth is saturated with NaCl and extracted with ethyl acetate (5×100 mL). The combined organic extract is dried over $Na_2SO_4$, filtered, and concentrated. Silica gel chromatography yields (2R,3S,4S,5R)-2,4-dimethyl-3,5-dihydroxy-n-heptanoic acid 6-lactone.

This method provides a means for large-scale production of novel modular polyketides containing unnatural starter units, uncontaminated by the polyketide containing the native propionate starter unit.

The cell-free results reported here, in conjunction with the availability of facile mutagenesis tools, provide a novel approach to the study of modular PKS structure and mechanisms. The considerable yield of fully active protein from the recombinant source described will permit detailed analysis of this multifunctional catalyst by radioisotopic methods as well as by NMR and mass spectroscopy. Given that DEBS can accept a variety of substrates as primers, it will be possible to make quantitative assessments of substrate specificity by determination of the relevant steady state kinetic parameters and to further probe mechanistic details. In addition, cell-free systems such as the one reported here provide a completely novel route for the controlled synthesis of novel polyketides which might otherwise not be accessible via in vivo engineered biosynthesis.

Thus, novel methods for producing polyketides, are disclosed. Although preferred embodiments of the subject invention have been described in some detail, it is understood that obvious variations can be made without departing from the spirit and the scope of the invention as defined by the appended claims.

What is claimed is:

1. A method to produce a desired polyketide which method comprises:
   (a) providing a functional modular polyketide synthase (PKS) comprising at least a first and second module wherein said PKS has been modified to prevent its utilization of a native starter unit for said modular PKS by inactivation of the catalytic domain of the ketosynthase of said first module, but wherein said PKS is able to incorporate a diketide substrate into at least a triketide, and
   which PKS is a complete erythromycin PKS gene cluster, i.e., 6-deoxyerythronolide B (6-dEB) synthase;
   (b) adding to said modified PKS a diketide that is a substrate for the modified PKS;
   (c) incubating the modified PKS and said diketide under conditions wherein said polyketide is synthesized; and
   (d) optionally recovering the polyketide.

2. The method of claim 1 wherein said modified PKS is contained in host cells.

3. The method of claim 2 wherein said cells are heterologous to said modified PKS, and/or
   wherein said cells are Streptomyces; and/or
   wherein said cells are permeable to said diketide; and/or
   wherein said cells have been modified to delete a native PKS contained in said cells.

4. The method of claim 3 wherein said cells are S. coelicolor CH999.

5. The method of claim 1 which is conducted in a cell free system.

6. The method of claim 1 wherein the diketide is that obtained by the coupling of a starter unit which is acetyl CoA, malonamyl Co-A, propionyl Co-A, butyryl Co-A, isobutyryl Co-A, isovaleryl Co-A, benzoyl Co-A, aminobenzoyl Co-A, aminohydroxybenzoyl Co-A, or thiophene carboxyl Co-A, with an extender unit which is malonyl Co-A, methylmalonyl Co-A or ethylmalonyl Co-A.

7. The method of claim 6 wherein the diketide is that obtained by the coupling of a starter unit which is malonamyl Co-A, butyryl Co-A, isobutyryl Co-A, isovaleryl Co-A, benzoyl Co-A, aminobenzoyl Co-A, or aminohydroxybenzoyl Co-A with an extender unit which is methylmalonyl Co-A or ethylmalonyl Co-A.

8. The method of claim 7 wherein the diketide is that obtained by the coupling of a starter unit which is malonamyl Co-A, butyryl Co-A, isobutyryl Co-A or isovaleryl Co-A with an extender unit which is methylmalonyl Co-A.

9. The method of claim 8 wherein the diketide is that obtained by the coupling of a starter unit which is butyryl Co-A with an extender unit which is methylmalonyl Co-A.

10. A polyketide prepared by the method of claim 7.
11. A polyketide prepared by the method of claim 8.
12. A polyketide prepared by the method of claim 9.
13. The polyketide of claim 12 which is 13-propyl-6-dEB.

* * * * *